(12) United States Patent
Lociuro et al.

(10) Patent No.: US 10,717,757 B2
(45) Date of Patent: Jul. 21, 2020

(54) KETOLIDES HAVING ANTIBACTERIAL ACTIVITY

(71) Applicant: BIOPHARMATI SA, Lugano (CH)

(72) Inventors: Sergio Lociuro, Lugano (CH); Khalid Islam, Lugano (CH)

(73) Assignee: Biopharmati SA, Manno (CH)

( * ) Notice: Subject to any disclaimer, the term of this patent is extended or adjusted under 35 U.S.C. 154(b) by 0 days.

(21) Appl. No.: 16/368,803

(22) Filed: Mar. 28, 2019

(65) Prior Publication Data
US 2019/0225640 A1 Jul. 25, 2019

Related U.S. Application Data

(63) Continuation of application No. PCT/US2017/055079, filed on Oct. 4, 2017.

(60) Provisional application No. 62/403,804, filed on Oct. 4, 2016.

(51) Int. Cl.
- *C07H 17/08* (2006.01)
- *C07D 498/04* (2006.01)
- *A61K 31/7048* (2006.01)
- *A61K 31/7042* (2006.01)
- *A61P 31/04* (2006.01)

(52) U.S. Cl.
CPC ......... *C07H 17/08* (2013.01); *A61K 31/7042* (2013.01); *A61K 31/7048* (2013.01); *A61P 31/04* (2018.01); *C07D 498/04* (2013.01)

(58) Field of Classification Search
CPC ..... C07H 17/08; A61P 31/04; A61K 31/7042; A61K 31/7048
See application file for complete search history.

(56) References Cited

U.S. PATENT DOCUMENTS

| | | | |
|---|---|---|---|
| 6,590,083 B1 * | 7/2003 | Hlasta | C07H 17/08 536/7.4 |
| 7,332,476 B2 | 2/2008 | Burger et al. | |
| 7,462,600 B2 | 12/2008 | Chupak et al. | |
| 2005/0009764 A1 * | 1/2005 | Burger | C07H 17/08 514/29 |
| 2005/0153905 A1 | 7/2005 | Burger et al. | |

FOREIGN PATENT DOCUMENTS

| | | |
|---|---|---|
| WO | 98/09978 A1 | 3/1998 |
| WO | 2014049356 A1 | 4/2014 |

OTHER PUBLICATIONS

Andreotti, D. et al "A novel ketolide class . . . " Bioorg. Med. Chem. Lett., vol. 17, pp. 5265-5269. (Year: 2007).*
Pubchem, Compound Summary for SID 79844006, Available date: Jun. 12, 2008 [retrieved on Nov. 8, 2017], Retrieved from the Internet: https://pubchem.ncbi.nlm.nih.gov/substance/79844006.
International Search Report dated Jan. 22, 2018 cited in PCT/US2017/055079.
Supplementary European Search Report cited in EP 17859090 dated May 15, 2020.

* cited by examiner

*Primary Examiner* — Leigh C Maier
(74) *Attorney, Agent, or Firm* — Perkins Coie LLP; Viola Kung

(57) ABSTRACT

The present invention relates to ketolide compounds of Formula I. The compounds have good anti-microbial activities, reduced inhibition of cytochrome $P_{450}3A4$ (CYP3A4), and acceptable safety of co-administration of other drugs. The present invention also relates to a pharmaceutical composition comprising compounds of Formula I and the method of treating anti-microbial infection by administering the compounds. Oral administration is a preferred route of administration.

5 Claims, No Drawings

KETOLIDES HAVING ANTIBACTERIAL ACTIVITY

This application is a continuation of PCT/US2017/055079, filed Oct. 4, 2017; which claims the benefit of U.S. Provisional Application No. 62/403,804, filed Oct. 4, 2016. The contents of the above-identified applications are incorporated herein by reference in their entirety.

FIELD OF THE INVENTION

The present invention relates to novel ketolide compounds that have good anti-microbial activities and reduced inhibition of cytochrome $P_{450}3A4$ (CYP3A4). The invention also relates to pharmaceutical compositions of the ketolide compounds, and their medical use.

BACKGROUND OF THE INVENTION

Microbial infections give rise to various diseases depending on the site of infection and the nature of the microorganism. In some cases, infection can lead to death, especially in the young, the elderly and in immuno-compromised individuals. Bacterial infections are primarily treated with antibiotics. However, the incidence of infections caused by antibiotic resistant microorganisms is on the increase. Antibiotic-resistant microorganisms cannot readily be treated with conventional antibiotics. Among the microorganisms known to have developed resistance to certain antibiotics are bacterial strains such as *Streptococcus pneumoniae*. The severity of such infections often requires immediate medical intervention and the treatment of patients by intravenous administration of antibiotics.

Cethromycin, also known as ABT-773, is a ketolide antibiotic that has shown promise in the treatment of microbial infections, for instance respiratory tract infections caused by macrolide-resistant microorganisms. While cethromycin may be used in the treatment of macrolide-resistant infections, it has certain drawbacks. Cethromycin exhibits strong inhibition of cytochrome $P_{450}3A4$ (CYP3A4), an important metabolic enzyme involved in the oxidation of xenobiotics in vivo. As a result of its strong CYP3A4 inhibition, cethromycin displays drug-drug interaction which causes problems during concomitant administration with other drugs metabolized by cytochrome P450 enzymes, i.e., CYP3A4. It has been estimated that CYP3A4 metabolizes about half of all drugs on the market and so the incompatibility associated with co-administration of cethromycin with other drugs is a problem. In vitro experiments with human liver microsomes and recombinant CYP isoforms indicate that cethromycin is metabolized to one primary metabolite (M-1) and two secondary metabolites. The M-1 metabolite is formed by CYP3A (both CYP3A4 and CYP3A5 are able to metabolize cethromycin). Further in vitro work demonstrated that cethromycin was able to inhibit CYP3A-dependent nifedipine oxidation with an $IC_{50}$ of 0.63 µM (482.5 ng/mL). (see Katz et al, Clin Pharmacol Ther. 75:516-28, (2004); and Cethromycin for the Treatment of Community-Acquired Bacterial Pneumonia, FDA Briefing Document for Anti-Infective Drugs Advisory Committee Meeting, Jun. 2, 2009, wayback.archive-it.org/7993/20170405205229/https://www.fda.gov/downloads/AdvisoryCommittees/CommitteesMeetingMaterials/Drugs/AntiInfectiveDrugsAdvisoryCommittee/UCM161847.pdf)

Solithromycin is a ketolide antibiotic undergoing clinical development for the treatment of community-acquired pneumonia and other infections. Solithromycin exhibits excellent in vitro activity against a broad spectrum of Gram-positive respiratory tract pathogens, including macrolide-resistant strains. Solithromycin is both a CYP3A4 and P-gp substrate, and is also a strong inhibitor of CYP3A4 and a moderate inhibitor of P-gp. The drug-drug interaction profile of solithromycin is consistent with that of previously approved macrolides. Solithromycin should not be administered to patients who are receiving strong or moderate CYP3A/P-gp inducers because of the risk of subtherapeutic exposure and loss of efficacy. Concomitant administration of solithromycin with sensitive CYP3A and/or P-gp substrates that have potential adverse effects due to increased plasma concentrations (e.g. digoxin) may require monitoring and/or dose adjustment of the concomitantly administered drug. The profile for potential drug-drug interactions is consistent with that of other macrolides. (see Solithromycin For The Treatment Of Community Acquired Bacterial Pneumonia, Briefing Document For The Antimicrobial Drugs, Advisory Committee Meeting Date: Nov. 4, 2016, www.fda.gov/downloads/AdvisoryCommittees/CommitteesMeetingMaterials/Drugs/Anti-InfectiveDrugsAdvisoryCommittee/UCM527691.pdf).

There is a need for new drugs that display adequate antimicrobial properties similar to cethromycin against susceptible and/or resistant strains such as *S. Pneumonia*, but have limited ability to inhibit CYP3A4 in order to improve the safety of drug co-administration.

DETAILED DESCRIPTION OF THE INVENTION

Definitions

An "enantiomer" is one of two stereoisomers that are mirror images of each other that are non-superimposable (not identical). Organic compounds that contain a chiral carbon usually have two non-superimposable structures.

"Pharmaceutically acceptable salts," as used herein, are salts that retain the desired biological activity of the parent compound and do not impart undesired toxicological effects. Pharmaceutically acceptable salt forms include various crystalline polymorphs as well as the amorphous form of the different salts. The pharmaceutically acceptable salts can be formed with metal or organic counterions and include, but are not limited to, alkali metal salts such as sodium or potassium; alkaline earth metal salts such as magnesium or calcium; and ammonium or tetraalkyl ammonium salts, i.e., $NX_4+$(wherein X is $C_{1-4}$).

A "Racemate" is a mixture that has equal amounts of left- and right-handed enantiomers of a chiral molecule.

"Solvates," as used herein, are addition complexes in which the compound is combined with an acceptable co-solvent in some fixed proportion. For the compound of the present invention, co-solvents include, but are not limited to, water, ethanol, and acetic acid.

Ketolide Compounds

The inventors have isolated and identified compounds of Formula I or a pharmaceutically acceptable salt, solvate, an enantiomer, or enantiomers thereof. The compounds or their pharmaceutically acceptable salts, solvates, enantiomers, or enantiomers have adequate anti-microbial activities and have reduced inhibition of cytochrome $P_{450}3A4$ (CYP3A4) comparing with cethromycin, thus the compounds have reduced drug-drug interactions and have improved the safety of co-administration with other drugs. The compounds of Formula I have potency against macrolide-resistant respiratory tract pathogens, while maintain enhanced gastric stability and broad spectrum activity. Compounds of Formula I have the following general structure:

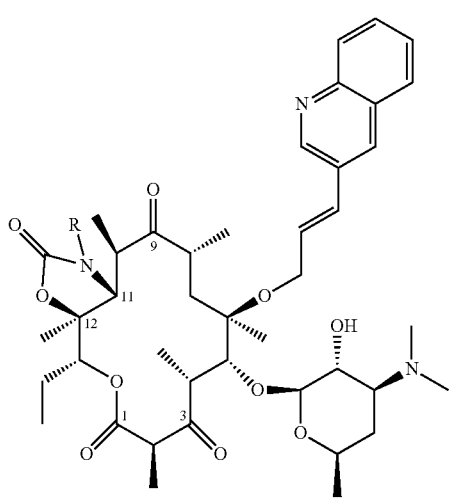

Formula I Compounds wherein R=—(CH$_2$)$_2$N(CH$_2$CH$_3$)$_2$ (Compound 13A), —(CH$_2$)$_3$N(CH$_3$)$_2$ (13B), —(CH$_2$)$_2$OCH$_3$ (Compound 13E), —(CH$_2$)$_2$N(CH$_2$CH$_3$)(CH$_3$) (Compound 13G), —CH$_2$CN (Compound 13H), Compound 13C Compound 13D Compound 13I Compound 13J Compound 13K Compound 13L Compound 13M Compound 13N Compound 13P Compound 13Q Compound 13A:
(3aS,4R,7R,9R,10R,11R,13R,15R,15aR)-1-[2-(diethylamino)ethyl]-10{[(2S,3R,4S,6R)-4-(dimethylamino)-3-hydroxy-6-methyloxan-2-yl]oxy}-4-ethyl-3a,7,9,11,13,15-hexamethyl-11-{[(2E)-3-(quinolin-3-yl)prop-2-en-1-yl]oxy}-tetradecahydro-1H-oxacyclotetradeca[4,3-d][1,3]oxazole-2,6,8,14-tetrone Compound 13B:
(3aS,4R,7R,9R,10R,11R,13R,15R,15aR)-10-{[(2S,3R,4S,6R)-4-(dimethylamino)$_3$-hydroxy-6-methyloxan-2-yl]oxy}-1-[3-(dimethylamino)propyl]-4-ethyl-3a,7,9,11,13,15-hexamethyl-11-{[(2E)-3-(quinolin-3-yl)prop-2-en-1-yl]oxy}tetradecahydro-1H-oxacyclotetradeca[4,3-d][1,3]oxazole-2,6,8,14-tetrone Compound 13C:
(3aS,4R,7R,9R,10R,11R,13R,15R,15aR)-10-{[(2S,3R,4S,6R)-4-(dimethylamino)-3-hydroxy-6-methyloxan-2-yl]oxy}-4-ethyl-1-{[(2S)-1-ethylpyrrolidin-2-yl]methyl}-3a,7,9,11,13,15-hexamethyl-11-{[(2E)-3-(quinolin-3-yl)prop-2-en-1-yl]oxy}-tetradecahydro-1H-oxacyclotetradeca[4,3-d][1,3]oxazole-2,6,8,14-tetrone Compound 13D
(3aS,4R,7R,9R,10R,11R,13R,15R,15aR)-10-{[(2S,3R,4S,6R)-4-(dimethylamino)-3-hydroxy-6-methyloxan-2-yl]oxy}-4-ethyl-1-{[(2R)-1-ethylpyrrolidin-2-yl]methyl}-3a,7,9,11,13,15-hexamethyl-11-{[(2E)-3-(quinolin-3-yl)prop-2-en-1-yl]oxy}-tetradecahydro-1H-oxacyclotetradeca[4,3-d][1,3]oxazole-2,6,8,14-tetrone Compound 13E:
(3aS,4R,7R,9R,10R,11R,13R,15R,15aR)-10-{[(2S,3R,4S,6R)-4-(dimethylamino)-3-hydroxy-6-methyloxan-2-yl]oxy}-4-ethyl-1-(2-methoxyethyl)-3a,7,9,11,13,15-hexamethyl-11-{[(2E)-3-(quinolin-3-yl)prop-2-en-1-yl]oxy}-tetradecahydro-1H-oxacyclotetradeca[4,3-d][1,3]oxazole-2,6,8,14-tetrone Compound 13F (Comparative Compound):
(3aS,4R,7R,9R,10R,11R,13R,15R,15aR)-10-{[(2S,3R,4S,6R)-4-(dimethylamino)-3-hydroxy-6-methyloxan-2-yl]oxy}-1-[2-(dimethylamino)ethyl]-4-ethyl-3a,7,9,11,13,15-hexamethyl-11-{[(2E)-3-(quinolin-3-yl)prop-2-en-1-yl]oxy}-tetradecahydro-1H-oxacyclotetradeca[4,3-d][1,3]oxazole-2,6,8,14-tetrone Compound 13G:
(3aS,4R,7R,9R,10R,11R,13R,15R,15aR)-10-{[(2S,3R,4S,6R)-4-(dimethylamino)-3-hydroxy-6-methyloxan-2-yl]oxy}-4-ethyl-1-{2-[ethyl(methyl)amino]ethyl}-3a,7,9,11,13,15-hexamethyl-11-{[(2E)-3-(quinolin-3-yl)prop-2-en-1-yl]oxy}-tetradecahydro-1H-oxacyclotetradeca[4,3-d][1,3]oxazole-2,6,8,14-tetrone Compound 13H:
2-[(3aS,4R,7R,9R,10R,11R,13R,15R,15aR)-10-{[(2S,3R,4S,6R)-4-(dimethylamino)-3-hydroxy-6-methyloxan-2-yl]oxy}-4-ethyl-3a,7,9,11,13,15-hexamethyl-2,6,8,14-tetraoxo-11-{[(2E)-3-(quinolin-3-yl)prop-2-en-1-yl]oxy}-tetradecahydro-1H-oxacyclotetradeca[4,3-d][1,3]oxazol-1-yl]acetonitrile Compound 13I:
(3aS,4R,7R,9R,10R,11R,13R,15R,15aR)-10-{[(2S,3R,4S,6R)-4-(dimethylamino)-3-hydroxy-6-methyloxan-2-yl]oxy}-4-ethyl-3a,7,9,11,13,15-hexamethyl-1-[2-(pyrrolidin-1-yl)ethyl]-11-{[(2E)-3-(quinolin-3-yl)prop-2-en-1-yl]oxy}-tetradecahydro-1H-oxacyclotetradeca[4,3-d][1,3]oxazole-2,6,8,14-tetrone Compound 13J:
(3aS,4R,7R,9R,10R,11R,13R,15R,15aR)-10-{[(2S,3R,4S,6R)-4-(dimethylamino)-3-hydroxy-6-methyloxan-2-yl]oxy}-4-ethyl-3a,7,9,11,13,15-hexamethyl-1-[3-(morpholin-4-yl)propyl]-11-{[(2E)-3-(quinolin-3-yl)prop-2-en-1-yl]oxy}-tetradecahydro-1H-oxacyclotetradeca[4,3-d][1,3]oxazole-2,6,8,14-tetrone Compound 13K:
(3aS,4R,7R,9R,10R,11R,13R,15R,15aR)-10-{[(2S,3R,4S,6R)-4-(dimethylamino)-3-hydroxy-6-methyloxan-2-yl]oxy}-4-ethyl-3a,7,9,11,13,15-hexamethyl-1-[2-(4-methylpiperazin-1-yl)ethyl]-11-{[(2E)-3-(quinolin-3-yl)prop-2-en-1-yl]oxy}-tetradecahydro-1H-oxacyclotetradeca[4,3-d][1,3]oxazole-2,6,8,14-tetrone Compound 13L:
(3aS,4R,7R,9R,10R,11R,13R,15R,15aR)-10-{[(2S,3R,4S,6R)-4-(dimethylamino)-3-hydroxy-6-methyloxan-2-yl]oxy}-4-ethyl-3a,7,9,11,13,15-hexamethyl-1-[(1-methylpiperidin-4-yl)methyl]-11-{[(2E)-3-(quinolin-3-yl)prop-2-en-1-yl]oxy}-tetradecahydro-1H-oxacyclotetradeca[4,3-d][1,3]oxazole-2,6,8,14-tetrone Compound 13M:
(3aS,4R,7R,9R,10R,11R,13R,15R,15aR)-1-[3-(azetidin-1-yl)propyl]-10-{[(2S,3R,4S,6R)-4-(dimethylamino)-3-hydroxy-6-methyloxan-2-yl]oxy}-4-ethyl-3a,7,9,11,13,15-hexamethyl-11-{[(2E)-3-(quinolin-3-yl)prop-2-en-1-yl]oxy}-tetradecahydro-1H-oxacyclotetradeca[4,3-d][1,3]oxazole-2,6,8,14-tetrone Compound 13N:
(3aS,4R,7R,9R,10R,11R,13R,15R,15aR)-10-{[(2S,3R,4S,6R)-4-(dimethylamino)-3-hydroxy-6-methyloxan-2-yl]oxy}-4-ethyl-3a,7,9,11,13,15-hexamethyl-1-{[(3S)-1-methylpyrrolidin-3-yl]methyl}-11-{[(2E)-3-(quinolin-3-yl)prop-2-en-1-yl]oxy}-tetradecahydro-1H-oxacyclotetradeca[4,3-d][1,3]oxazole-2,6,8,14-tetrone Compound 13P:
(3aS,4R,7R,9R,10R,11R,13R,15R,15aR)-10-{[(2S,3R,4S,6R)-4-(dimethylamino)-3-hydroxy-6-methyloxan-2-yl]oxy}-4-ethyl-3a,7,9,11,13,15-hexamethyl-1-{2-[(2R)-1-methylpyrrolidin-2-yl]ethyl}-11-{[(2E)-3-(quinolin-3-yl)prop-2-en-1-yl]oxy}-tetradecahydro-1H-oxacyclotetradeca[4,3-d][1,3]oxazole-2,6,8,14-tetrone Compound 13Q:
(3aS,4R,7R,9R,10R,11R,13R,15R,15aR)-10-{[(2S,3R,4S,6R)-4-(dimethylamino)-3-hydroxy-6-methyloxan-2-yl]oxy}-4-ethyl-3a,7,9,11,13,15-hexamethyl-1-{2-[(2S)-1-methylpyrrolidin-2-yl]ethyl}-11-{[(2E)-3-(quinolin-3-yl)prop-2-en-1-yl]oxy}-tetradecahydro-1H-oxacyclotetradeca[4,3-d][1,3]oxazole-2,6,8,14-tetrone Formula I compounds possess desirable antibacterial properties, i.e., ability to inhibit bacterial growth and/or ability to kill bacteria as expressed. Formula I compounds particularly have antibacterial properties against *Streptococcus pneumoniae*, particularly antibiotic resistant strains thereof, e.g., macrolide-resistant and/or penicillin-resistant strains. Formula I compounds preferably have reduced inhibition of CYP3A4 comparing with cethromycin, thus the compounds have reduced drug-drug interactions and have improved the safety of co-administration with other drugs.

Compound 13B has demonstrated an excellent oral bioavailability and tissue distribution; drug level in the lungs remained elevated for at least 8 hours after a single oral treatment. Compound 13B has demonstrated efficacy in mouse lung infection models against macrolide-resistant *S. pneumoniae* strains.

Synthesis of Compounds of Formula I

To prepare Formula I compounds, an intermediate Compound 11 is prepared first from Compound 7 (Plata et al, *tetrahedron*, 60: 10171-10180, 2004, see Compounds 9b-9d at page 10173), according to the scheme below.

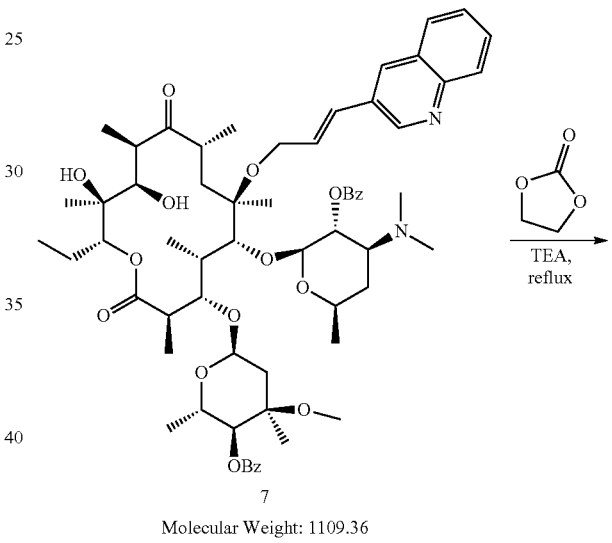

7
Molecular Weight: 1109.36

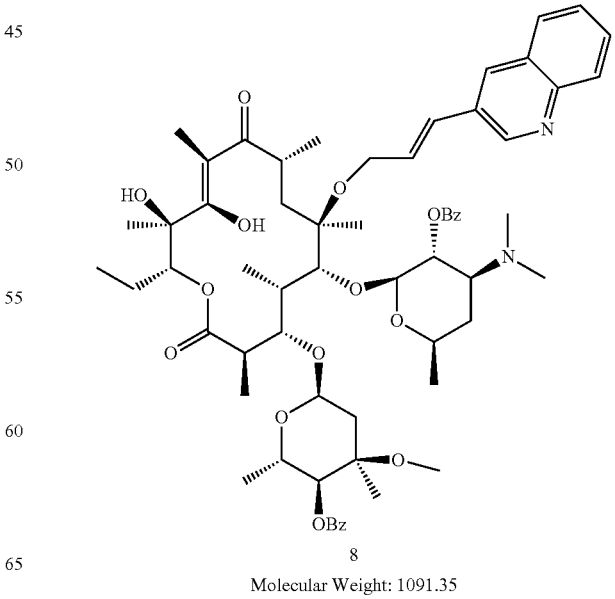

8
Molecular Weight: 1091.35

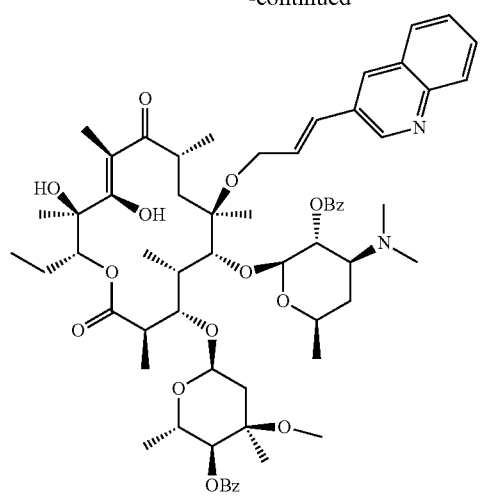

8
Molecular Weight: 1091.35

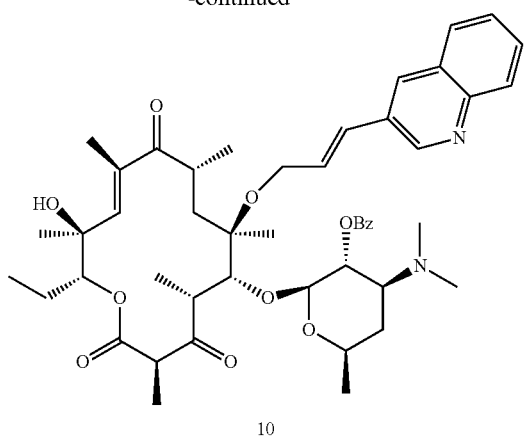

10
Molecular Weight: 827.03

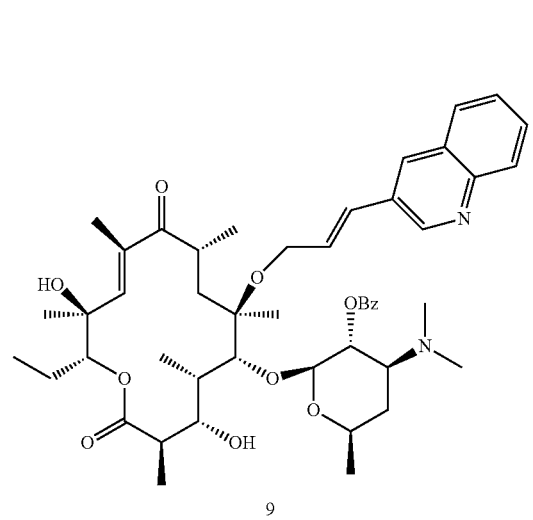

9
Molecular Weight: 829.04

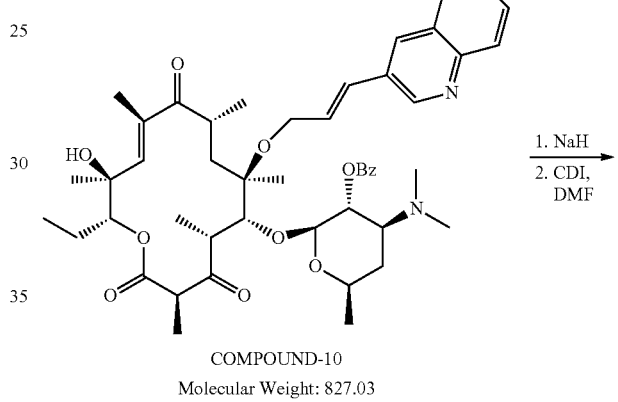

COMPOUND-10
Molecular Weight: 827.03

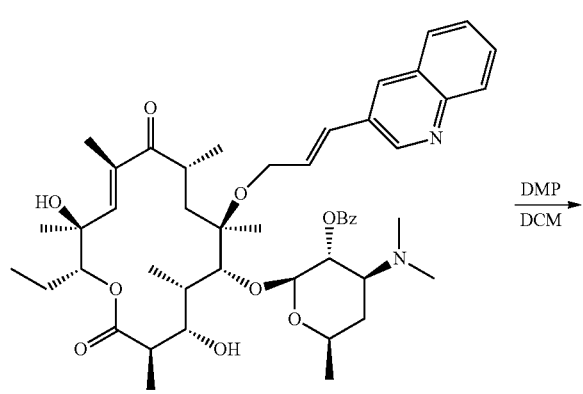

9
Molecular Weight: 829.04

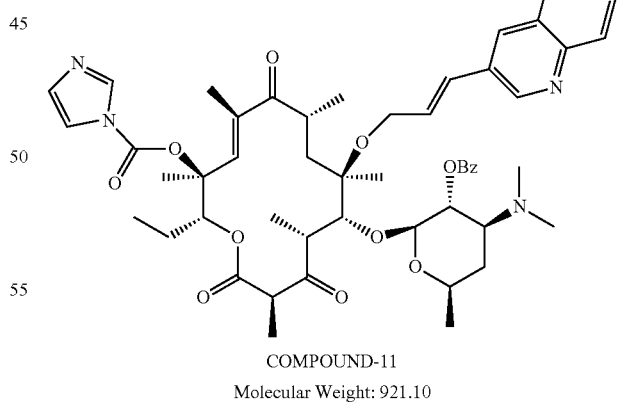

COMPOUND-11
Molecular Weight: 921.10

Intermediate Compound 11 is then reacted with NH$_2$—R in acetonitrile and water to form Compound 12 with a protected group OBz. Compound 12 is then added with methanol and heated to remove the protected group to yield Compound 13. The synthesis schemes from Compound 11 to Compound 13 are illustrated below.

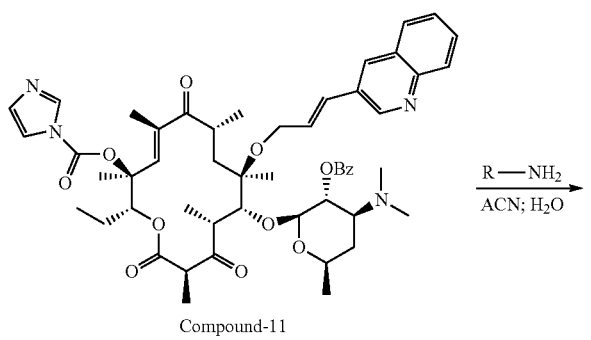

Compound-11
Molecular Weight: 921.10

R—NH$_2$
ACN; H$_2$O

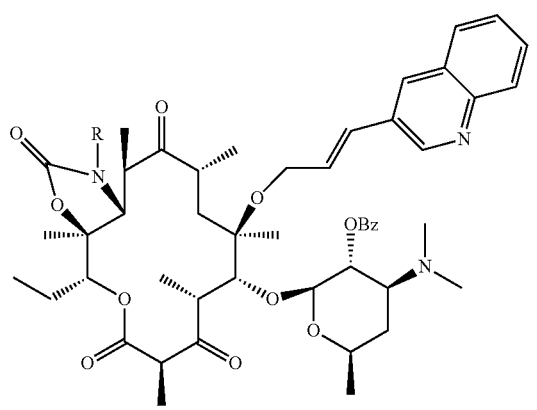

Compound-12
Molecular Weight: 884.08

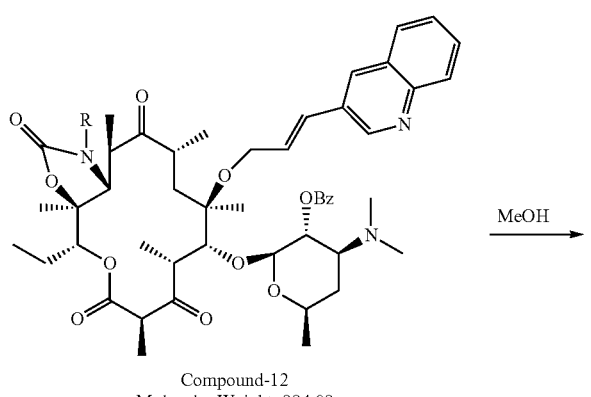

Compound-12
Molecular Weight: 884.08

MeOH

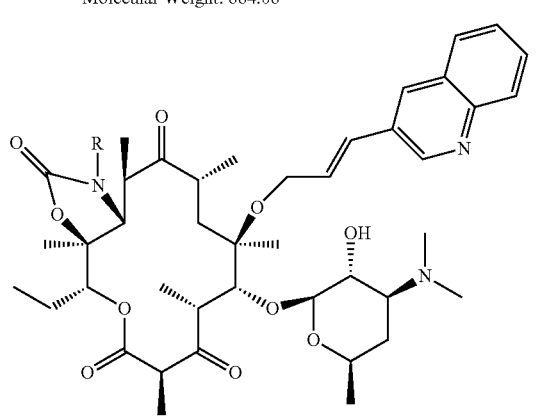

Compound-13
Molecular Weight: 779.97

Pharmaceutical Compositions

The present invention provides pharmaceutical compositions comprising one or more pharmaceutically acceptable carriers and a compound of Formula I, or a pharmaceutically acceptable salt, or an enantiomer, or enantiomers thereof. The pharmaceutical composition can include one of the enantiomers, or both enantiomers either equimolar as a racemate, or of different amounts. For abbreviation, "an active compound," when used in this application, is meant to include a Formula I compound, or a pharmaceutically acceptable salt, or an enantiomer, or enantiomers thereof. The active compound in the pharmaceutical compositions in general is in an amount about 1-90% for a tablet formulation, 1-100% for a capsule formulation, about 0.1-5% for an injectable formulation, about 0.01-20%, (w/w) for a topical formulation.

In one embodiment, the pharmaceutical composition can be in a dosage form such as tablets, capsules, granules, fine granules, powders, syrups, suppositories, injectable solutions, patches, or the like. In another embodiment, the active compound is incorporated into any acceptable carrier, including creams, gels, lotions or other types of suspensions that can stabilize the active compound and deliver it to the affected area by topical applications. The above pharmaceutical composition can be prepared by conventional methods.

Pharmaceutically acceptable carriers, which are inactive ingredients, can be selected by those skilled in the art using conventional criteria. The pharmaceutically acceptable carriers may contain ingredients that include, but are not limited to, saline and aqueous electrolyte solutions; ionic and non-ionic osmotic agents such as sodium chloride, potassium chloride, glycerol, and dextrose; pH adjusters and buffers such as salts of hydroxide, phosphate, citrate, acetate, borate; and trolamine; antioxidants such as salts, acids and/or bases of bisulfite, sulfite, metabisulfite, thiosulfite, ascorbic acid, acetyl cysteine, cysteine, glutathione, butylated hydroxyanisole, butylated hydroxytoluene, tocopherols, and ascorbyl palmitate; surfactants such as lecithin, phospholipids, including but not limited to phosphatidylcholine, phosphatidylethanolamine and phosphatidyl inositiol; poloxamers and poloxamines, polysorbates such as polysorbate 80, polysorbate 60, and polysorbate 20, polyethers such as polyethylene glycols and polypropylene glycols; polyvinyls such as polyvinyl alcohol and povidone; cellulose derivatives such as methylcellulose, hydroxypropyl cellulose, hydroxyethyl cellulose, carboxymethyl cellulose and hydroxypropyl methylcellulose and their salts; petroleum derivatives such as mineral oil and white petrolatum; fats such as lanolin, peanut oil, palm oil, soybean oil; mono-, di-, and triglycerides; polymers of acrylic acid such as carboxypolymethylene gel, and hydrophobically modified cross-linked acrylate copolymer; polysaccharides such as dextrans and glycosaminoglycans such as sodium hyaluronate. Such pharmaceutically acceptable carriers may be preserved against bacterial contamination using well-known preservatives, these include, but are not limited to, benzalkonium chloride, ethylenediaminetetraacetic acid and its salts, benzethonium chloride, chlorhexidine, chlorobutanol, methylparaben, thimerosal, and phenylethyl alcohol, or may be formulated as a non-preserved formulation for either single or multiple use.

For example, a tablet formulation or a capsule formulation of the active compound may contain other excipients that have no bioactivity and no reaction with the active compound. Excipients of a tablet or a capsule may include fillers, binders, lubricants and glidants, disintegrators, wetting agents, and release rate modifiers. Binders promote the adhesion of particles of the formulation and are important for a tablet formulation. Examples of excipients of a tablet or a capsule include, but not limited to, carboxymethylcellulose, cellulose, ethylcellulose, hydroxypropylmethylcellulose, methylcellulose, karaya gum, starch, tragacanth gum, gelatin, magnesium stearate, titanium dioxide, poly(acrylic acid), and polyvinylpyrrolidone. For example, a tablet formulation may contain inactive ingredients such as colloidal silicon dioxide, crospovidone, hypromellose, magnesium stearate, microcrystalline cellulose, polyethylene glycol, sodium starch glycolate, and/or titanium dioxide. A capsule formulation may contain inactive ingredients such as gelatin, magnesium stearate, and/or titanium dioxide.

For example, a patch formulation of the active compound may comprise some inactive ingredients such as 1,3-butylene glycol, dihydroxyaluminum aminoacetate, disodium edetate, D-sorbitol, gelatin, kaolin, methylparaben, polysorbate 80, povidone, propylene glycol, propylparaben, sodium carboxymethylcellulose, sodium polyacrylate, tartaric acid, titanium dioxide, and purified water. A patch formulation may also contain skin permeability enhancer such as lactate esters (e.g., lauryl lactate) or diethylene glycol monoethyl ether.

Topical formulations including the active compound can be in a form of gel, cream, lotion, liquid, emulsion, ointment, spray, solution, and suspension. The inactive ingredients in the topical formulations for example include, but not limited to, diethylene glycol monoethyl ether (emollient/permeation enhancer), DMSO (solubility enhancer), silicone elastomer (rheology/texture modifier), caprylic/capric triglyceride, (emollient), octisalate, (emollient/UV filter), silicone fluid (emollient/diluent), squalene (emollient), sunflower oil (emollient), and silicone dioxide (thickening agent).

Method of Use

According to the present invention, bacterial infections are treated or prevented in a patient by administering to the patient a therapeutically effective amount of a compound of Formula I, in such amounts and for such time as is necessary to achieve the desired result. By a "therapeutically effective amount," it is meant a sufficient amount of the compound to treat bacterial infections. It will be understood, however, that the total daily usage of the compounds and compositions of the present invention will be decided by the attending physician within the scope of sound medical judgement. The specific therapeutically effective dose level for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

The pharmaceutical composition of the present invention can be applied by local administration and systemic administration. Systemic administration includes oral, parenteral (such as intravenous, intramuscular, subcutaneous or rectal), and other systemic routes of administration. In systemic administration, the active compound first reaches plasma and then distributes into target tissues. Local administration includes topical administration.

Dosing of the composition can vary based on the extent of the injury and each patient's individual response. For systemic administration, plasma concentrations of the active compound delivered can vary; but are generally $1\times10^{-10}$-$1\times10^{-4}$ moles/liter, and preferably $1\times10^{-8}$-$1\times10^{-5}$ moles/liter.

In one embodiment, the pharmaceutical composition is administrated orally to the subject. The dosage for oral administration is generally at least 10 mg/day and less than 2000 mg/day in a single dose or multiple doses. For example, the dosage for oral administration is 20-200, or 50-500, or 200-2000 mg/day for a human subject.

In one embodiment, the pharmaceutical composition is administrated intravenously to the subject. The dosage for intravenous bolus injection or intravenous infusion is generally 50 to 1500 mg/day and preferably 100 to 800 mg/day in a single injection or repeated doses.

In one embodiment, the pharmaceutical composition is administrated subcutaneously to the subject. The dosage for subcutaneous administration is generally 50 to 1500 mg/day and preferably 100 to 800 mg/day in a single injection or repeated doses.

In one embodiment, the pharmaceutical composition is administrated by inhalation to the lungs of the subject. The dosage for inhaled administration is generally 50 to 1500 mg/day and preferably 100 to 800 mg/day in a single inhalation or repeated doses.

Those of skill in the art will recognize that a wide variety of delivery mechanisms are also suitable for the present invention.

Formula I compounds may be used with additional therapeutic agents by simultaneous, sequential, or separate administration. The additional therapeutic agents for example include anti-inflammatory agents and other antimicrobial agents, especially antibiotic agents.

The present invention is useful in treating a mammal subject, such as humans, horses, cows, cats, and dogs. The present invention is particularly useful in treating humans.

The following examples further illustrate the present invention. These examples are intended merely to be illustrative of the present invention and are not to be construed as being limiting.

EXAMPLES

Abbreviations aq. Aqueous
CFU colony forming unit
DCM dichloromethane
DIPEA diisopropylethylamine
DME 1,2-dimethoxyethane
DMSO dimethyl sulfoxide
EDC 1-(3-dimethylaminopropyl)-3-ethylcarbodiimide hydrochloride
eq equivalent(s)
Et$_3$N triethylamine
EA ethyl acetate
EtOH ethanol
h hour(s)
HOBt 1-hydroxy-benzotriazole
MeOH methanol
min minute(s)
MS mass spectrometry
N normality
NMR nuclear magnetic resonance spectrometry
Rf retention factor
RT room temperature
THF tetrahydrofuran
ACN Acetonitrile
TLC thin layer chromatography

Example 1. Synthesis of Intermediate Compound 11

A. Synthesis of Compound 8

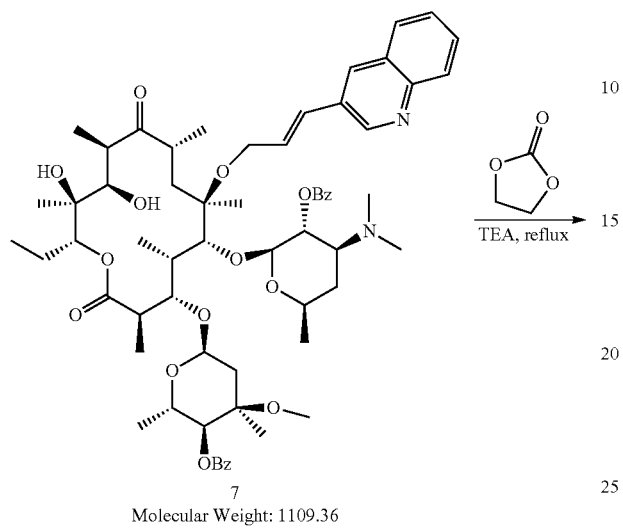

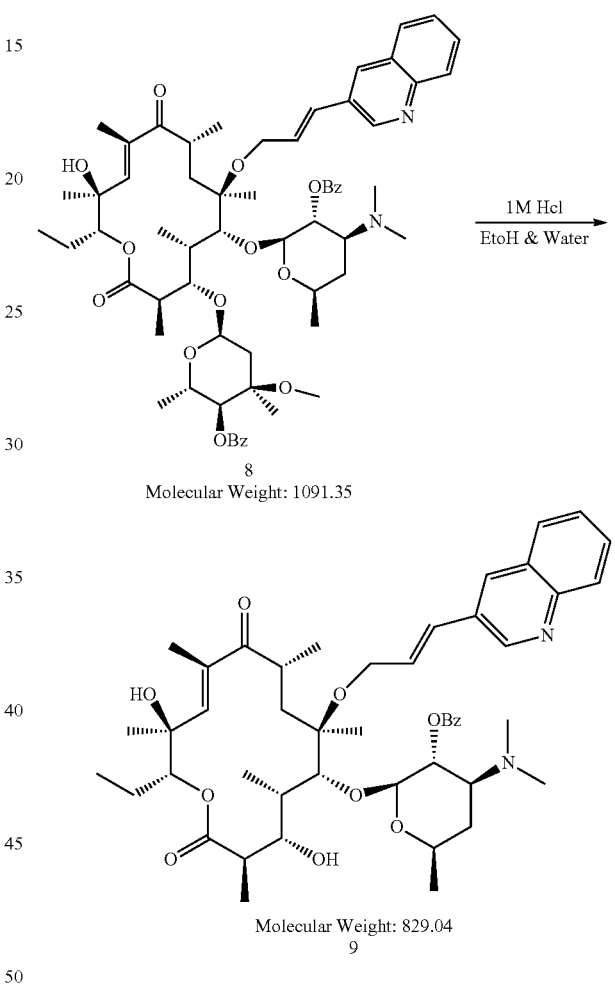

Compound 7 was prepared starting from commercially available erythromycin A oxime according to the protocols described in Plata et al (tetrahedron, 60: 10171-10180, 2004, see Compounds 9b-9d at page 10173).

Into a clean and dried 2 L three necked round-bottomed flask equipped with overhead stirrer and reflux condenser, compound 7 (140 gm, 0.12623 moles), 560 ml of TEA and ethylene carbonate (166 gm, 1.89 moles) were added. The solution was heated to 90° C. and maintained for 6 hrs. Reaction was monitored by TLC using 20% EA:DCM: 2 drops of ammonia. After reaction completion, the reaction was quenched with 1500 ml of water and extracted with 3×500 ml of ethyl acetate. Total organic layer was washed with 3×300 ml of brine and then dried over sodium sulfate. Concentration was done under reduced pressure to yielded 150 g of crude compound 8 (30% by HPLCA), which was taken as it was for the next step.

B. Synthesis of Compound 9

| Sl No | Raw materials | Wt (gm) | M. Wt | Moles | Eq | Source |
|---|---|---|---|---|---|---|
| 1 | Comp-7 | 140 gm | 1109.3 | 0.12623 | 1 | Step-6 |
| 2 | Ethylene carbonate | 166 gm | 88 | 1.89 | 15 | spectrochem |
| 3 | TEA | 560 ml | | | 4 vol | SDFCL |

| Sl No | Raw materials | Wt (gm) | M. Wt | Moles | Eq | Source |
|---|---|---|---|---|---|---|
| 1 | Comp-8 | 150 gm | 1091.3 | 0.1374 | 1 | Step-7 |
| 2 | 1M HCl | 600 ml | | | 4 vol | SD Fine chem |
| 3 | Ethanol | 600 ml | | | 4 vol | Advent |
| 4 | Water | 600 ml | | | 4 vol | |

Into a clean and dried 2l three necked round-bottomed flask equipped with overhead stirrer and reflux condenser, Compound 8 (150 gm, 0.1374 moles), 600 ml of 1 M HCl, 600 ml of Ethanol and 600 ml of distilled water were added. The solution was heated to 55° C. and maintained for 6 hrs. Reaction was monitored by TLC using 20% EA:DCM: two drops of ammonia. After completion of the reaction, ethanol was concentrated and the aqueous layer was extracted with 3×450 ml of ethyl acetate (for removing of all undesired impurities). The aqueous layer was basified with solid potassium carbonate to pH 8-9 at 0° C. and the obtained precipitate was extracted with 3×450 ml of ethyl acetate. The combined organic layers were washed with 3×300 ml of brine, dried over sodium sulfate and concentrated under reduced pressure to get 85 gm crude product. Obtained crude product was purified by basic alumina using 1% Methanol: DCM to yield 55 g of 60% pure compound 9.

C. Synthesis of Compound 10

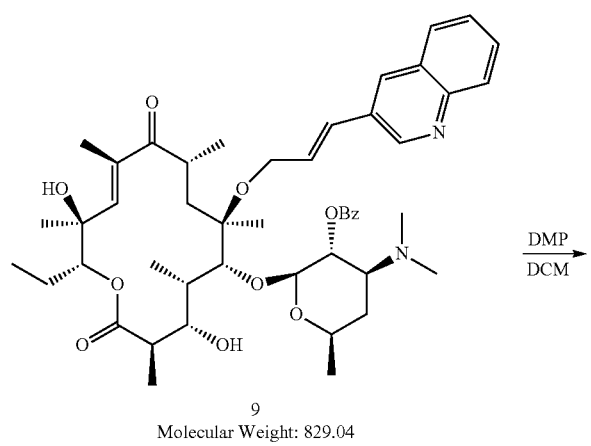

9
Molecular Weight: 829.04

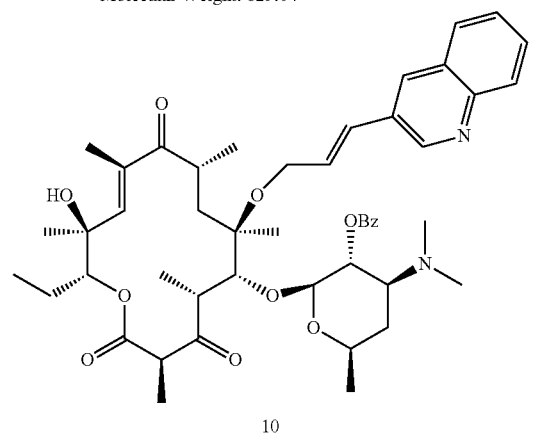

10
Molecular Weight: 827.03

| Sl No | Raw materials | Wt (gm) | M. Wt | Moles | Eq | Source |
|---|---|---|---|---|---|---|
| 1 | Comp-9 | 55 gm | 8290.4 | 0.06634 | 1 | Step-8 |
| 2 | Dess martin periodinane | 59 gm | 424 | 0.1393 | 2.1 | Spectrochem |
| 3 | DCM | 550 ml | | | 10 vol | |

Into a clean and dried 1 l three necked round-bottomed flask equipped with magnetic stirrer, Compound 9 (55 gm, 0.06634 moles) and 550 ml of DCM were added. The solution was cooled to 0° C. and added Dess martin periodinane at 0° C. over a period of 30 min. The reaction was monitored by TLC using 20% EA:DCM: two drops of ammonia. After completion of the reaction, it was diluted with 500 ml of DCM, washed with 3×250 ml of 1 N NaOH, dried over anhydrous sodium sulfate and concentrated under reduced pressure to get 35 g of crude compound which was dissolved in diethyl ether and the organic layer was washed with 1N NaOH solution, dried over anhydrous sodium sulfate and concentrated under reduced pressure to yield 27 g compound 10 with 50% HPLC purity.

D. Synthesis of Compound 11

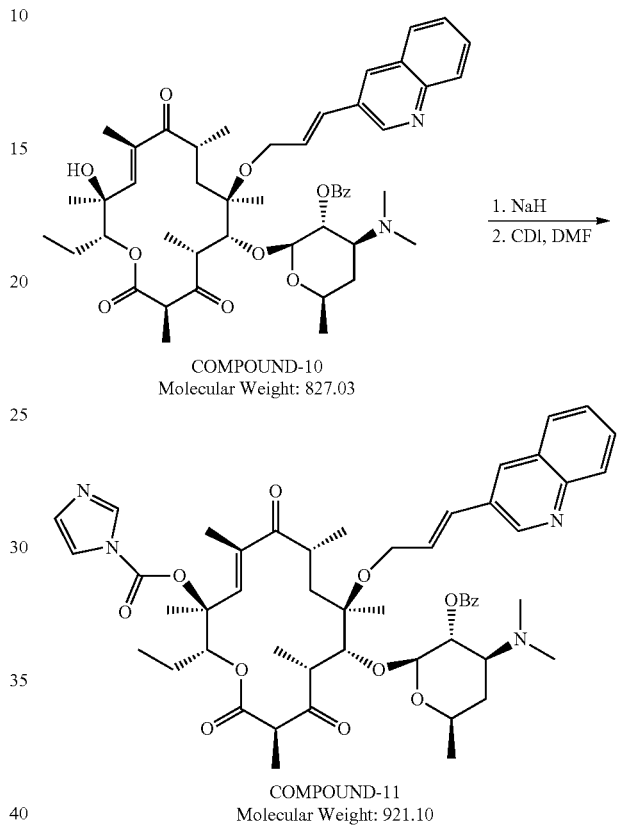

COMPOUND-10
Molecular Weight: 827.03

COMPOUND-11
Molecular Weight: 921.10

| Sl No | Raw materials | Wt (gm) | M. Wt | Moles | Eq | Source |
|---|---|---|---|---|---|---|
| 1 | Compound-10 | 3.0 gm | 827 | 0.0036 | 1.0 | In-house |
| 2 | NaH (60%) | 0.15 gm | 24 | 0.0062 | 3.0 | Spectrochem |
| 3 | CDI | 2.0 gm | 162.2 | 0.0126 | 3.5 | Spectrochem |
| 4 | DMF | 45 ml | | | 15 vol | Merck |

Into a clean and dried 100 ml two necked round-bottomed flask equipped with magnetic stirrer and nitrogen set up, DMF (15 ml), and sodium hydride (150 mg) were added. After cooling at 10-15° C., compound-10, dissolved in 15 ml of DMF was added drop wise using dropping funnel at the same temperature. The temperature was allowed to rise to RT and was maintained for 20 min. The reaction mass was cooled to 10-15° C. and solid carbonyl di imidazole (2.0 gm, 0.0126 mol) was added. The temperature was maintained for 30 min at RT and the reaction was monitored by TLC using 50% EA:Hexane. After completion of the reaction, it was quenched with 50 ml of ice cold distilled water at 10-15° C. and extracted with 2×60 ml of ethyl acetate. Total organic layer was washed with 2×50 ml brine solution, dried over anhydrous sodium sulfate and concentrated under reduced pressure to yield 3.5 g of crude compound 11 which was taken as it was for next step.

Example 2. Synthesis of Compound 13A from Compound 11

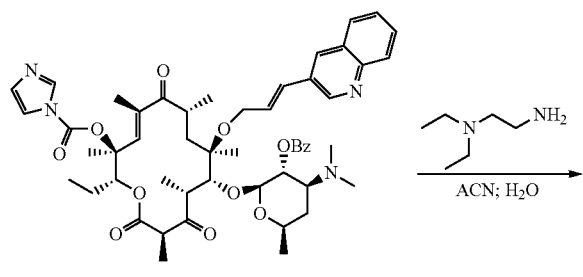

Compound-11
Molecular Weight: 921.10

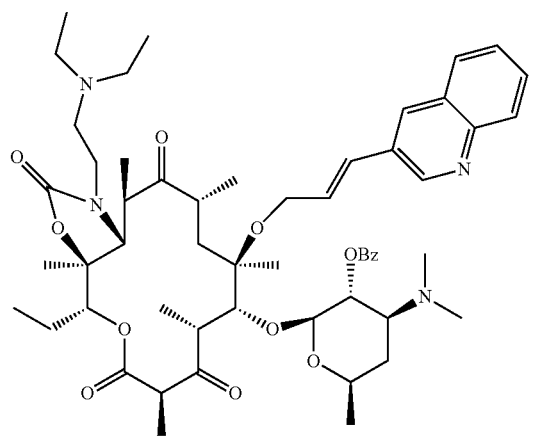

Compound-12 A
Molecular Weight: 969.23

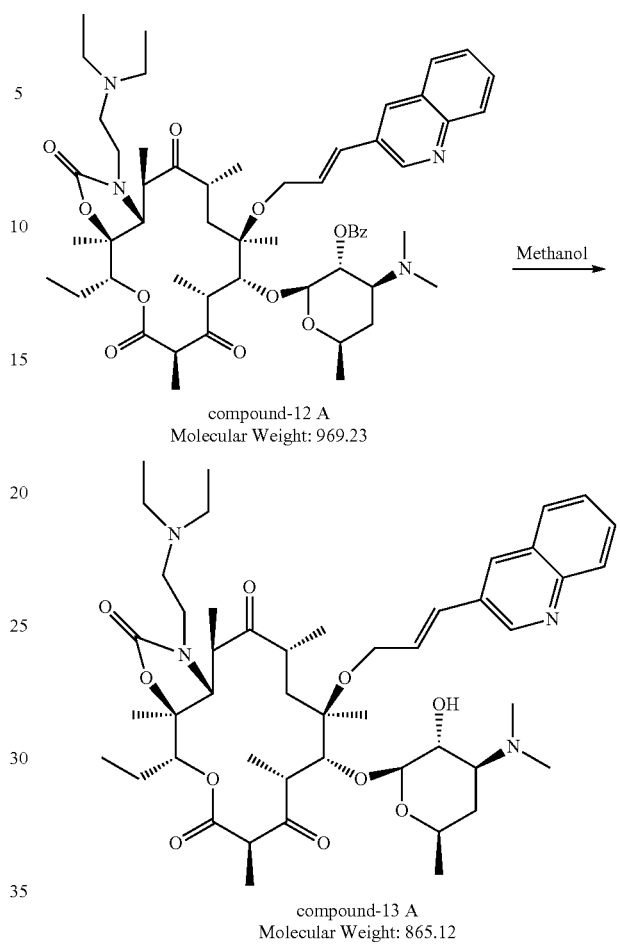

compound-12 A
Molecular Weight: 969.23 compound-13 A
Molecular Weight: 865.12

| Sl No | Raw materials | Wt (gm) | M. Wt | Moles | Eq | Source |
|---|---|---|---|---|---|---|
| 1 | Compound-11 | 3.5 gm | 921.10 | 0.0038 | 1.0 | In house |
| 2 | N,N-diethyleth-ane-1,2-di-amine | 6.62 gm | 116.21 | 0.057 | 15 | TCI Pharma |
| 3 | Acetonitrile | 30 ml | | | 9 vol | spectro-chem |
| 4 | Water | 5.0 ml | | | 1 vol | |

Into a clean and dried 100 ml two necked round-bottomed flask equipped with magnetic stirrer and nitrogen set up, Compound 11 (3.1 gm, 0.0033 mol), 35 ml of 1:1 of ACN; water mixture, and N,N-diethylethane-1,2-diamine (5.867 gm, 0.050 mol) were added at RT. The reaction mixture was heated at 65° C. and the temperature maintained for 6 h. Reaction was monitored by TLC using 40% ethyl acetate in hexane. After completion of the reaction, it was concentrated and quenched with 50 ml of ice cold water at 10-15° C. and the precipitated solid was filtered and dried to yield 4 g of Crude Compound 12A, which was taken as it was for next step (81% HPLC).

| Sl No | Raw materials | Wt (gm) | M. Wt | Moles | Eq | Source |
|---|---|---|---|---|---|---|
| 1 | Compound-12 A | 4.0 gm | 969.23 | 0.00412 | 1.0 | In house |
| 2 | Methanol | 40 ml | — | — | 10 vol | |

Into a clean and dried 100 ml two necked round-bottomed flask equipped with magnetic stirrer and nitrogen set up, Compound 12A (4.0 gm, 0.00412 mol) and 40 ml of methanol were added and the solution was heated at 65° C. and maintained for 4 hrs. The reaction was monitored by TLC using 10% MeOH in DCM. After completion of the reaction, it was concentrated and quenched with 50 ml of ice cold water, extracted with 2×40 ml of ethyl acetate. The combined organic layers were washed with 2×25 ml Brine solution, dried over sodium sulfate and concentrated to yield 2 g of crude compound which was purified by two times prep purification to yield 300 mg of the desired compound 13A (yield; 12% from compound 11 to 13A).

1H NMR (DMSO, 300 MHz): 9.0 (d, 1H, J=3), 8.21 (s, 1H), 7.92-8.0 (m, 2H), 7.69-7.74 (m, 1H), 7.57-7.62 (m, 1H), 6.64-6.69 (m, 1H), 6.25-6.30 (m, 1H), 4.09-5.00 (m, 1H), 4.16-4.31 (m, 4H), 3.79-3.84 (m, 2H), 3.61 (s, 1H), 3.88-3.48 (m, 3H), 2.16-2.40 (m, 12H), 1.48-1.59 (m, 6H), 1.29-1.37 (m, 6H), 0.95-1.23 (m, 16H), 0.68-0.93 (m, 13H)

Example 3. Synthesis of Compound 13B

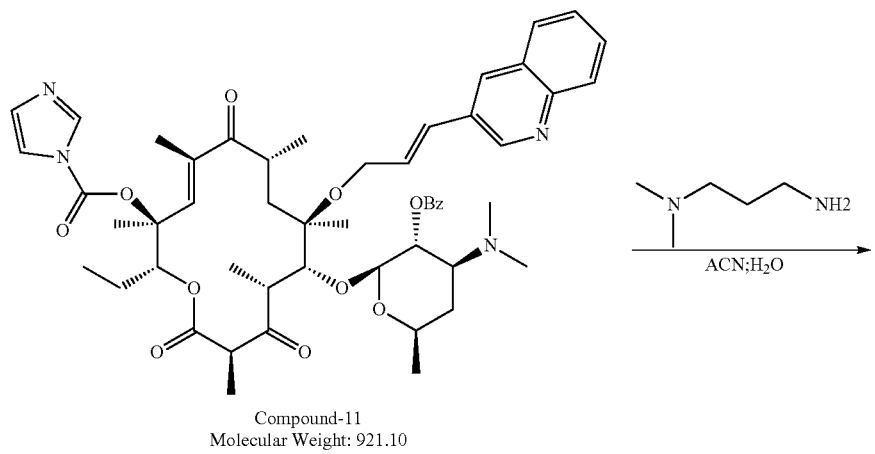

Compound-11
Molecular Weight: 921.10

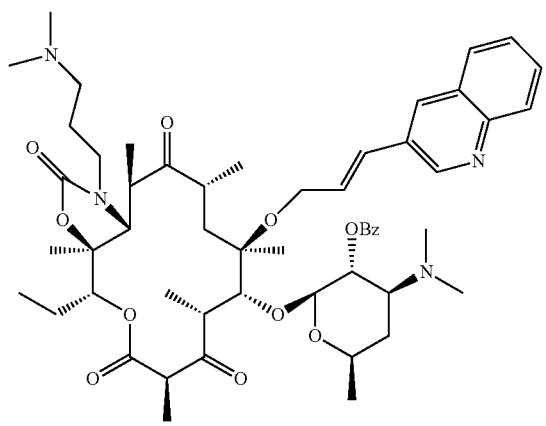

Compound-12B
Molecular Weight: 955.20

| Sl No | Raw materials | Wt (gm) | M. Wt | Moles | Eq | Source |
|---|---|---|---|---|---|---|
| 1 | Compound-11 | 3.5 gm | 921.1 | 0.0037 | 1.0 | In house |
| 2 | N,N-dimethylpro-pane-1,3-diamine | 7.47 gm | 131.1 | 0.057 | 15 | TCI Pharma |
| 3 | Acetonitrile | 31 ml | | | 9 vol | spectrochem |
| 4 | water | 4.0 ml | | | 1 vol | |

Into a clean and dried 100 ml two necked round-bottomed flask equipped with magnetic stirrer and nitrogen set up, Compound 11 (3.1 gm, 0.0037 mol), 35 ml of 1:1 ratio of ACN; water mixture and added N,N-dimethylpropane-1,3-diamine (7.47 gm, 0.057 mol) were added at RT. The solution was heated to 90° C. and maintained for 6 hrs. Reaction was monitored by TLC using 40% ethyl acetate in hexane. After completion of the reaction, it was concentrated and quenched with 35 ml of ice cold water. Filtered the solid precipitated and dried to yield 4 g of crude compound which was taken as it was for next step.

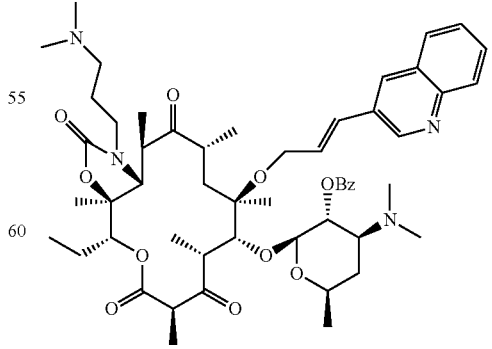

Compound-12B
Molecular Weight: 955.20

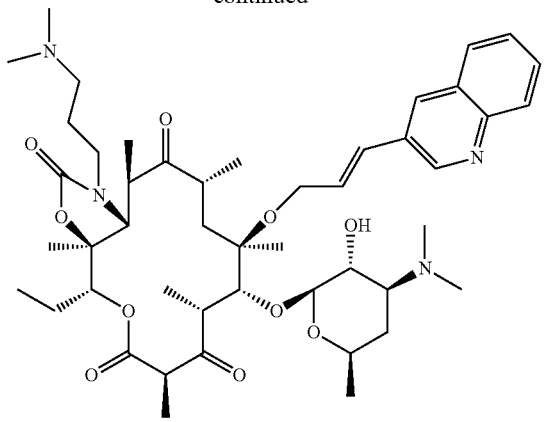

Compound-13B
Molecular Weight: 851.10

| Sl No | Raw materials | Wt (gm) | M. Wt | Moles | Eq | Source |
|---|---|---|---|---|---|---|
| 1 | Compound-12B | 4.0 gm | 969.23 | 0.00412 | 1.0 | In house |
| 2 | Methanol | 40 ml | — | — | 10 vol | |

Into a clean and dried 100 ml two necked round-bottomed flask equipped with magnetic stirrer and nitrogen set up, Compound 12B (4.0 gm, 0.00412 mol) and 40 ml of methanol were added. The solution was heated at 65° C. and maintained for 4 hrs. The reaction was monitored by TLC using 10% MeOH in DCM. After completion of the reaction, the reaction mass was concentrated and quenched with 40 ml of ice cold water; obtained precipitate was extracted with 2×40 ml of ethyl acetate. The combined organic layer was washed with 2×25 ml of brine solution, dried over sodium sulfate and concentrated under reduced pressure to yield 2.2 g of crude compound 13B, which was purified by prep HPLC (two times) to get 130 mg of Compound 13A with 93% HPLC purity (yield; 10% from compound 11 to 13B).

1H NMR (DMSO, 300 MHz): 9.1 (s, 1H), 8.22 (s, 1H), 7.92-8.00 (m, 2H), 7.69-7.74 (m, 1H), 7.57-7.62 (m, 1H), 6.63-6.69 (d, 1H), 6.25-6.31 (m, 1H), 4.86-4.89 (m, 1H), 4.17-4.36 (m, 4H), 3.70-3.84 (m, 2H), 3.61 (s, 1H), 3.04-3.34 (m, 4H), 2.16-2.26 (m, 7H), 1.98-2.08 (m, 2H), 1.72-1.89 (m, 8H), 1.45-1.54 (m, 7H), 1.30-1.38 (m, 7H), 1.17-1.23 (m, 8H), 1.10-1.15 (m, 3H), 0.80-0.88 (m, 8H)

Example 4. Synthesis of Compound 13C

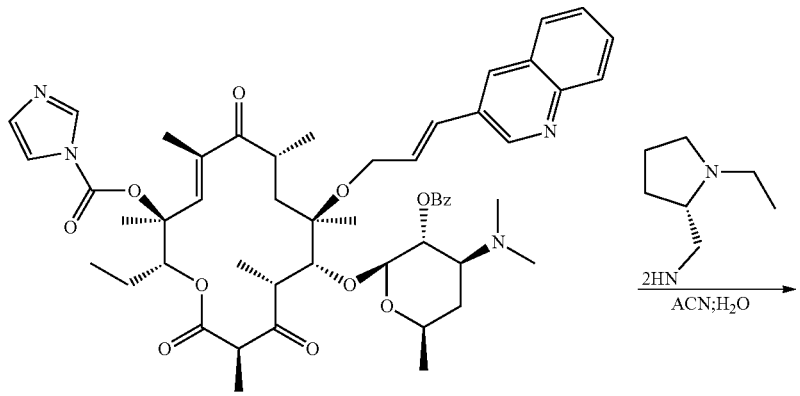

Compound-11
Molecular Weight: 921.10

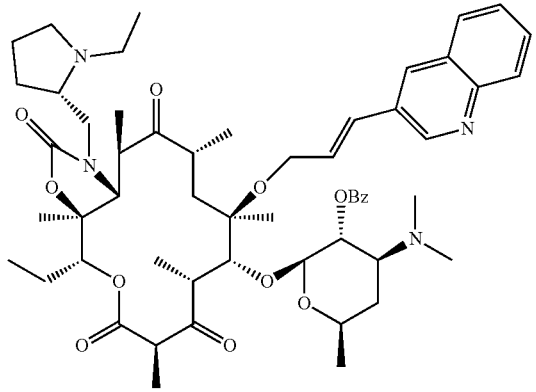

Compound-12 C
Molecular Weight: 981.24

| Sl No | Raw materials | Wt (gm) | M Wt | Moles | Eq | Source |
|---|---|---|---|---|---|---|
| 1 | Compound-11 | 3.0 gm | 921.10 | 0.0032 | 1.0 | In house |
| 2 | (R)-(1-eth-ylpyrrolidin-2-yl)meth-anamine | 6.26 gm | 128.22 | 0.097 | 15 | Combi blocks |
| 3 | Acetonitrile | 27 ml | | | 9 vol | spectrochem |
| 4 | Water | 3 ml | | | 1 vol | |

Into a clean and dried 100 ml two necked round-bottomed flask equipped with magnetic stirrer and nitrogen set up, Compound 11 (3.0 gm, 0.0032 mol), 40 ml 1:1 mixture of ACN:water and (R)-(1-ethylpyrrolidin-2-yl)methanamine (6.26 gm, 0.048 mol) were added at RT. The reaction mixture was heated at 65° C. and maintained for 6 hrs. The reaction was monitored by TLC using 60% ethyl acetate in hexane. After completion of the reaction, the reaction mass was concentrated and quenched with 30 ml of ice cold water and the obtained precipitate was extracted with ethyl acetate (3×50 ml), combined organic layers were dried over sodium sulfate and concentrated under reduced pressure to yield 4 g of crude compound 12C, which was taken as it was for next step.

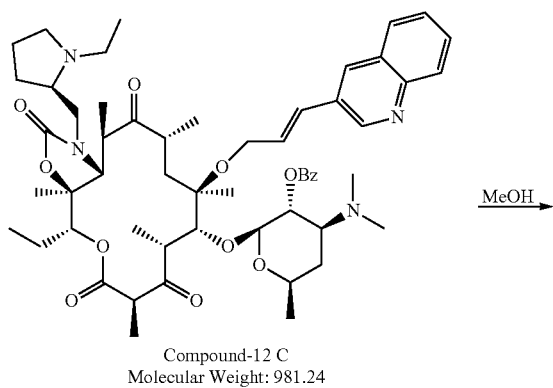

Compound-12 C
Molecular Weight: 981.24

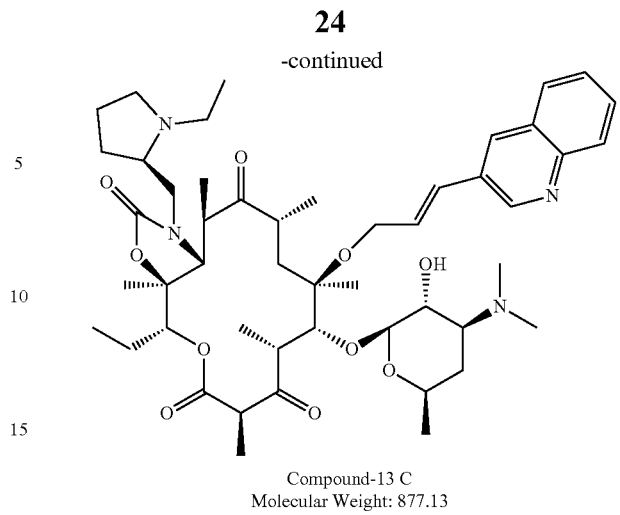

Compound-13 C
Molecular Weight: 877.13

| Sl No | Raw materials | Wt (gm) | M. Wt | Moles | Eq | Source |
|---|---|---|---|---|---|---|
| 1 | Compound-12 B | 4.0 gm | 981.24 | 0.004 | 1.0 | In house |
| 2 | Methanol | 40 ml | — | — | 10 vol | |

Into a clean and dried 100 ml two necked round-bottomed flask equipped with magnetic stirrer and nitrogen set up, compound 12C (10.0 gm, 0.010 mol) and 40 ml of methanol were added. The solution was heated at 65° C. and maintained for 4 hrs. The reaction was monitored by TLC using 10% MeOH in DCM. After completion of the reaction, reaction mass was concentrated under reduced pressure and quenched with 40 ml of ice cold water; obtained precipitate was extracted with 2×40 ml of ethyl acetate. Combined organic layers were washed with 2×25 ml of brine solution, dried over sodium sulfate and concentrated under reduced pressure to yield 2.5 g of crude compound which was purified by prep HPLC (two times) to yield 110 mg of Compound 13C with 90% HPLC purity (yield; 7% from compound 11 to 13C).

1H NMR (DMSO, 300 MHz): 9.03-9.04 (d, 1H, J=4 Hz), 8.21 (s, 1H), 7.91-8.00 (m, 2H), 7.69-7.73 (m, 1H), 7.57-7.61 (m, 1H), 6.65-6.69 (m, 1H), 6.28-6.32 (m, 1H), 5.0-5.12 (m, 1H), 4.1-4.36 (m, 5H), 3.81-3.86 (m, 2H), 3.75 (s, 1H), 2.50-3.34 (m, 4H), 2.23-2.43 (m, 4H), 1.87-2.16 (m, 5H), 1.46-1.85 (m, 10H), 1.25-1.38 (m, 9H), 0.93-1.19 (m, 15H), 0.81-0.85 (m, 7H)

Example 5. Synthesis of Compound 13D

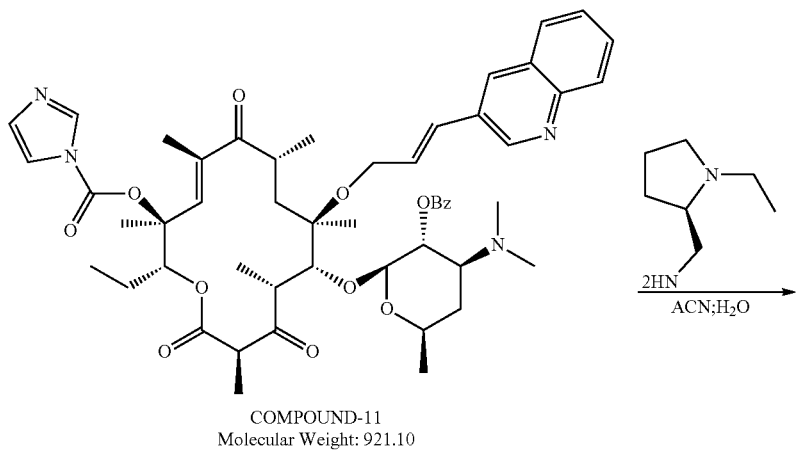

COMPOUND-11
Molecular Weight: 921.10

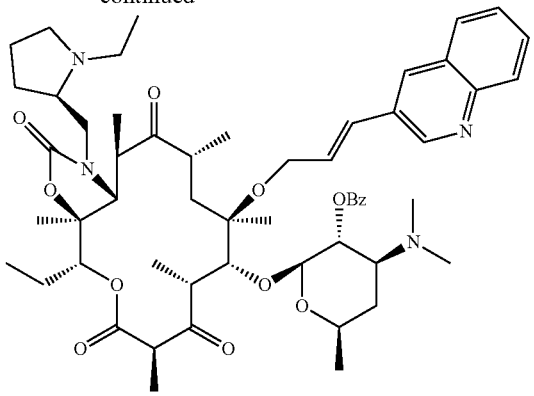

COMPOUND-12 D
Molecular Weight: 981.24

| Sl No | Raw materials | Wt (gm) | M. Wt | Moles | Eq | Source |
|---|---|---|---|---|---|---|
| 1 | Compound-11 | 6.0 gm | 921.10 | 0.0065 | 1.0 | In house |
| 2 | (S)-(1-ethylpyrrolidin-2-yl)methanamine | 12.52 gm | 128.22 | 0.097 | 15 | Combi blocks |
| 3 | Acetonitrile | 54 ml | | | 9 vol | spectrochem |
| 4 | water | 6 ml | | | 1 vol | |

Into a clean and dried 250 ml two necked round-bottomed flask quipped with magnetic stirrer and nitrogen set up, Compound 11 (6.0 gm, 0.0033 mol), 60 ml 1:1 mixture of ACN:water, (S)-(1-ethylpyrrolidin-2-yl)methaneamine (12.52 gm, 0.097 mol) were added at RT. The reaction mixture was hated at 65° C. and maintained for 6 hrs. The reaction was monitored by TLC using 60% ethyl acetate in hexane. After completion of the reaction, the reaction mass was concentrated and quenched with 60 ml of ice cold water and the obtained precipitate was extracted with ethyl acetate (3×60 ml), combined organic layers were dried over sodium sulfate and concentrated under reduced pressure to yield 10 g of crude Compound 12D, which was taken as it was for next step.

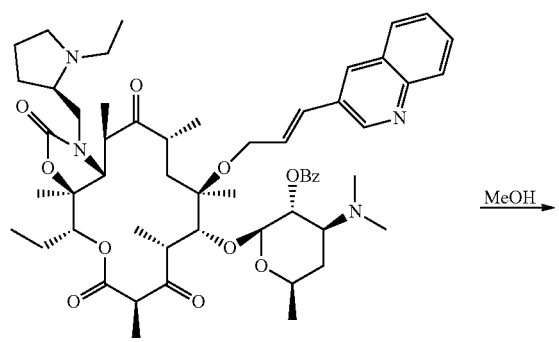

COMPOUND-12 D
Molecular Weight: 981.24

→ MeOH

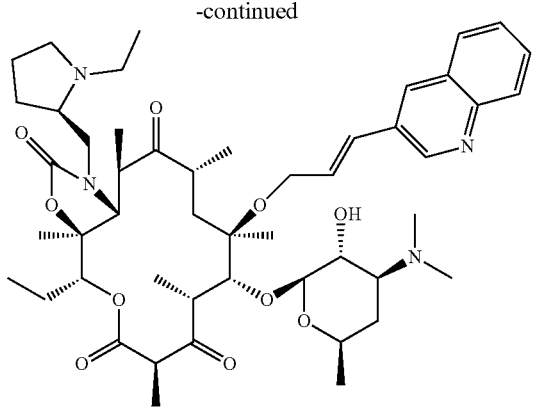

COMPOUND-13 D
Molecular Weight: 877.13

| Sl No | Raw materials | Wt (gm) | M. Wt | Moles | Eq | Source |
|---|---|---|---|---|---|---|
| 1 | Compound-12 B | 10.0 gm | 981.24 | 0.010 | 1.0 | In house |
| 2 | Methanol | 100 ml | — | — | 10 vol | |

Into a clean and dried 100 ml two necked round-bottomed flask equipped with magnetic stirrer and nitrogen set up, Compound 12D (10.0 gm, 0.010 mol) and 100 ml of methanol were added. The solution was heated at 65° C. and maintained for 4 hrs. The reaction was monitored by TLC using 10% MeOH in DCM. After completion of the reaction, the reaction mass was concentrated and quenched with 40 ml of ice cold water; obtained precipitate was extracted with 2×40 ml of ethyl acetate. Combined organic layers were washed with 2×25 ml of brine solution, dried over sodium sulfate and concentrated under reduced pressure to yield 6 g of crude compound which was purified by prep HPLC (two times) to get the desired compound 13D of 60 mg with 72% HPLC purity (yield; 5% from Compound 11 to 13D).

1H NMR (DMSO, 400 MHz): 9.04 (s, 1H), 8.23 (s, 1H), 7.90-7.99 (m, 2H), 7.712 (t, 1H, J=7.8 Hz), 7.59 (t, 1H, J=7.6 Hz), 6.63-6.67 (m, 1H), 6.25-6.29 (m, 1H), 4.91-4.93 (m, 1H), 4.16-4.34 (m, 5H), 3.63-3.92 (m, 4H), 2.66-2.70 (m, 3H), 2.20-2.44 (m, 5H), 1.69-1.82 (m, 4H), 1.60-1.64 (m, 6H), 1.36-1.46 (m, 12H), 1.03-1.29 (m, 14H), 0.71-0.88 (m, 10H)

Example 6. Synthesis of Compound 13E

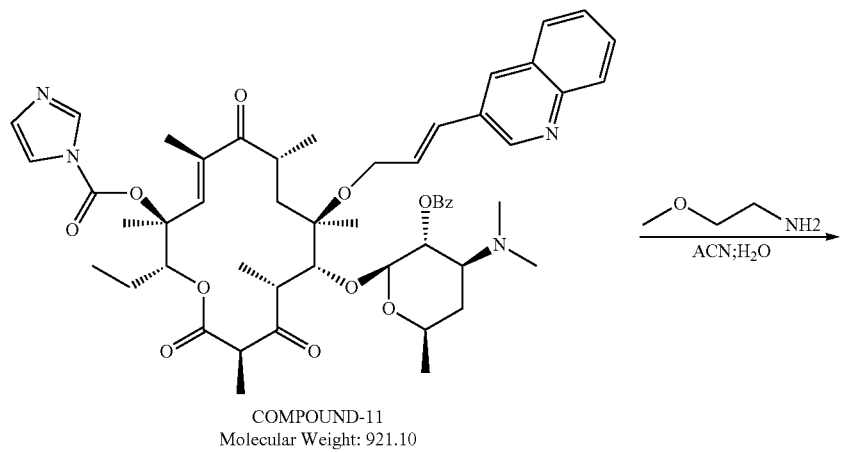

COMPOUND-11
Molecular Weight: 921.10

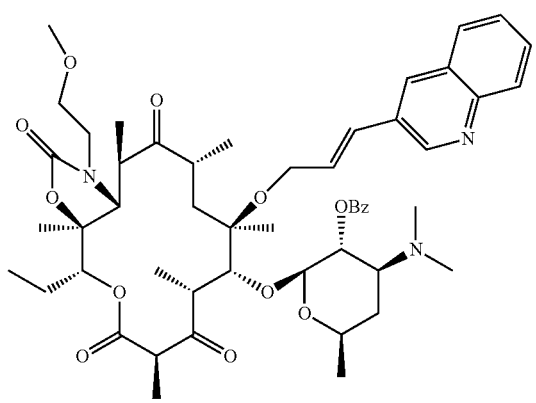

COMPOUND-12 E
Molecular Weight: 928.13

| Sl No | Raw materials | Wt (gm) | M. Wt | Moles | Eq | Source |
|---|---|---|---|---|---|---|
| 1 | Compound-11 | 3.0 gm | 921.10 | 0.0037 | 1.0 | In house |
| 2 | 2-methoxy-ethan-1-amine | 3.6 gm | 75.11 | 0.057 | 15 | Combi blocks |
| 3 | Acetonitrile | 31 ml | | | 9 vol | spectrochem |
| 4 | Water | 4.0 ml | | | 1 vol | |

Into a clean and dried 100 ml two necked round-bottomed flask equipped with magnetic stirrer and nitrogen set up, Compound 11 (6.0 gm, 0.0032 mol), 30 ml 1:1 mixture of ACN:water and 2-methoxyethan-1-amine (3.6 gm, 0.057 mol) were added at RT. The reaction mixture was heated at 65° C. and maintained for 6 hrs. The reaction mass was monitored by TLC using 60% ethyl acetate in hexane. After completion of the reaction, reaction mass was concentrated and quenched with 60 ml of ice cold water and the obtained precipitate was filtered and dried to yield 4 g of crude Compound 12E, which was taken as it was for next step.

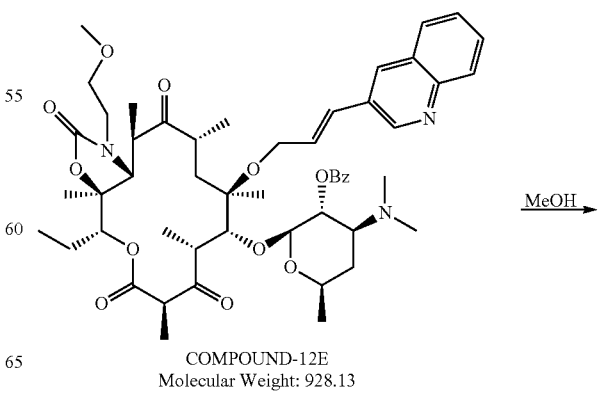

COMPOUND-12E
Molecular Weight: 928.13

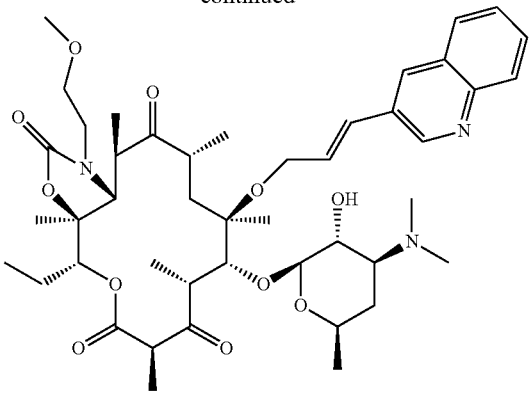

COMPOUND-13 E
Molecular Weight: 824.03

| Sl No | Raw materials | Wt (gm) | M. Wt | Moles | Eq | Source |
|---|---|---|---|---|---|---|
| 1 | Compound-12 E | 4.0 gm | 928.13 | 0.0043 | 1.0 | In house |
| 2 | Methanol | 40 ml | — | — | 10 vol | |

Into a clean and dried 100 ml two necked round-bottomed flask equipped with magnetic stirrer and nitrogen set up, Compound 12E (4.0 gm, 0.0043 mol) and 40 ml of methanol were added. The solution was heated at 65° C. and maintained for 4 hrs. The reaction was monitored by TLC using 10% MeOH in DCM. After completion of the reaction, reaction mass was concentrated under reduced pressure and quenched with 40 ml of ice cold water; obtained precipitate was extracted with 2×40 ml of ethyl acetate. Combined organic layers were washed with 2×25 ml of brine solution, dried over sodium sulfate and concentrated under reduced pressure to yield 2.5 g of crude compound which was purified by prep HPLC (two times) to get the desired Compound 13E of 400 mg with 95% HPLC purity (yield; 13% from Compound 11 to 13E).

1H NMR (DMSO, 400 MHz): 9.01-9.02 (d, 1H, J=Hz), 8.22 (s, 1H), 7.94-8.22 (m, 2H), 7.70-7.74 (m, 1H), 7.58-7.62 (m, 1H), 6.62-6.66 (d, 1H), 6.23-6.30 (m, 1H), 5.02-5.04 (m, 1H), 3.99-4.35 (m, 5H), 3.39-3.99 (m, 6H), 2.66-3.34 (m, 8H), 2.16-2.61 (m, 7H), 1.57-1.90 (m, 8H), 1.32-1.40 (m, 14H), 0.78-1.09 (m, 8H)

Example 7. Synthesis of Compound 13F (a Comparative Compound)

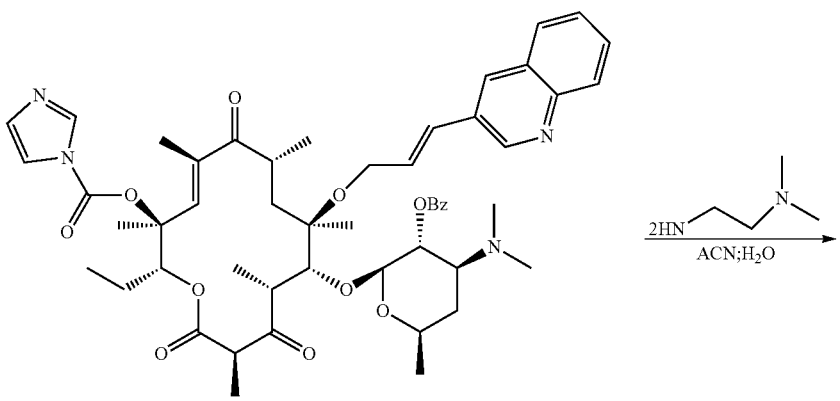

Compound 11
Molecular Weight: 921.10

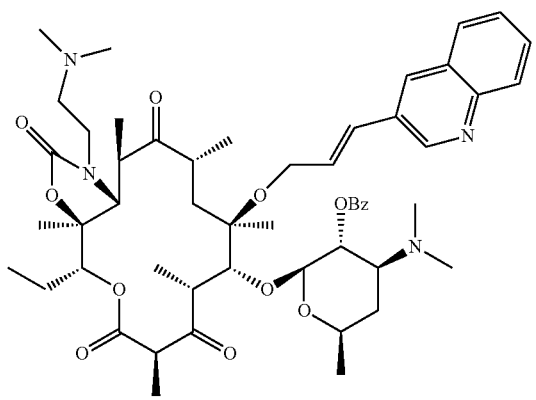

Compound 12F
Molecular Weight: 941.18

| Sl No | Raw materials | Wt (gm) | M. Wt | Moles | Eq | Source |
|---|---|---|---|---|---|---|
| 1 | Compound-11 | 3.5 gm | 921.10 | 0.0038 | 1.0 | In house |
| 2 | Dimethyl1,2-diamine | 4 gm | 88.15 | 0.0456 | 12 | Merck |
| 3 | Acetonitrile | 36 ml | | | 9 vol | |
| 4 | water | 4.0 ml | | | 1 vol | |

Into a clean and dried 100 ml two necked round-bottomed flask equipped with magnetic stirrer and nitrogen set up, Compound 11 (3.5 gm, 0.0038 mol), 35 ml 1:1 mixture of acetonitrile:water and dimethyl 1,2-diamine (4 gm, 0.0456 mole) were added at RT. The reaction mixture were heated at 65° C. and maintained for 6 hrs. The reaction was monitored by TLC using 60% ethyl acetate in hexane. After completion of the reaction, the reaction mass was concentrated and quenched with 60 ml of ice cold water and the obtained precipitate was filtered and dried to yield 4.2 g of crude Compound 12F, which was taken as it was for next step.

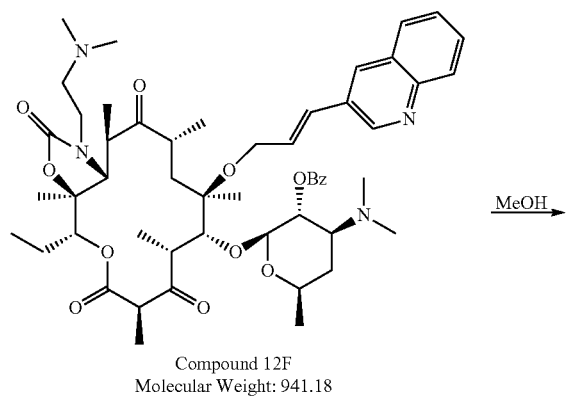

Compound 12F
Molecular Weight: 941.18

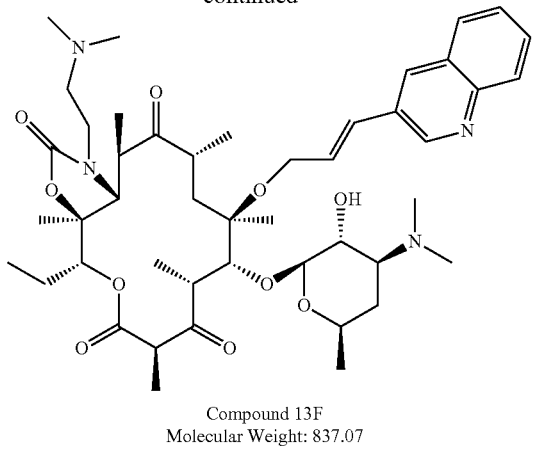

Compound 13F
Molecular Weight: 837.07

| Sl No | Raw materials | Wt (gm) | M.Wt | Moles | +Eq |
|---|---|---|---|---|---|
| 1 | Compound-12 F | 4.2 gm | 941 | 0.00446 | 1.0 |
| 2 | Methanol | 40 ml | — | — | 10 vol |

Into a clean and dried 100 ml two necked round-bottomed flask equipped with magnetic stirrer and nitrogen set up, Compound 12F (4.2 gm, 0.00446 mol) and 40 ml of methanol were added. The solution was heated at 65° C. and maintained for 4 hrs. The reaction was monitored by TLC using 10% MeOH in DCM. After completion of the reaction, reaction mass was concentrated and quenched with 40 ml of ice cold water; obtained precipitate was extracted with 2×40 ml of ethyl acetate. Combined organic layers were washed with 2×25 ml of brine solution, dried over sodium sulfate and concentrated under reduced pressure to yield 2.2 g of crude compound 13F which was purified by prep HPLC (two times) to get the desired compound 13F of 30 mg with 95% (87+8) HPLC purity (yield; 5% from Compound 11 to 13F).

1H NMR (DMSO, 400 MHz): 9.02 (s, 1H), 8.22 (s, 1H), 7.93-8.00 (m, 2H), 7.70-7.73 (m, 1H), 7.58-7.62 (m, 1H), 6.63-6.68 (d, 1H), 6.26-6.30 (m, 1H), 5.07-5.10 (m, 1H), 4.01-4.35 (m, 5H), 3.56-3.84 (m, 4H), 3.07-3.19 (m, 1H), 2.50-2.66 (m, 4H), 2.09-2.42 (m, 5H), 1.88-1.98 (m, 6H), 1.35-1.60 (m, 15H), 1.16-1.22 (m, 9H), 1.03-1.10 (m, 4H), 0.94-0.95 (m, 3H), 0.79-0.83 (m, 3H)

Example 8. Synthesis of Compound 13G

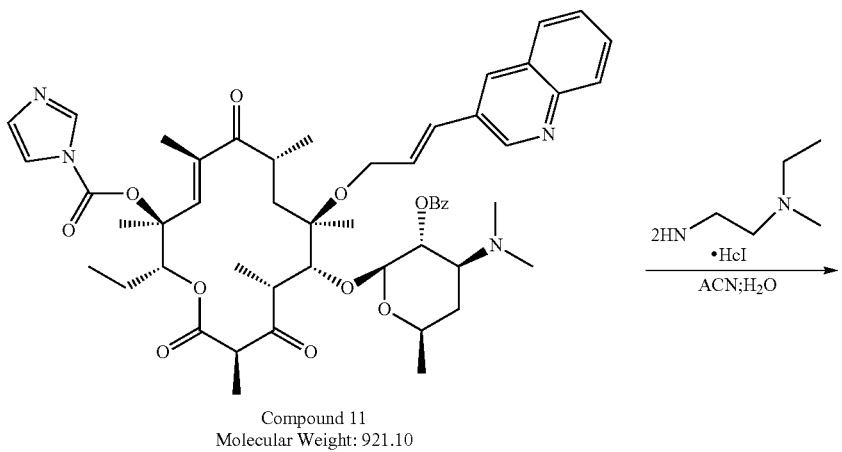

Compound 11
Molecular Weight: 921.10

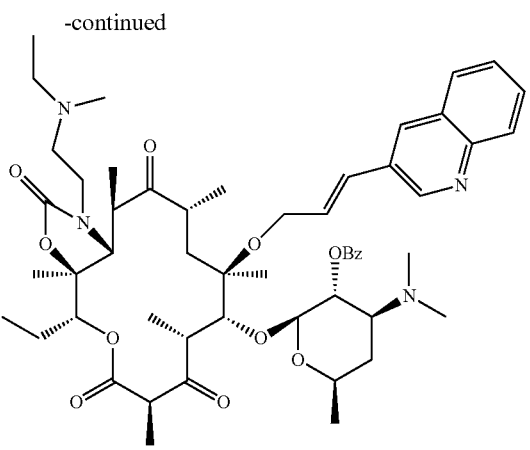

Compound 12G
Molecular Weight: 955.20

| Sl No | Raw materials | Wt (gm) | M. Wt | Moles | Eq | Source |
|---|---|---|---|---|---|---|
| 1 | Compound-11 | 4 gm | 921.10 | 0.0043 | 1.0 | In house |
| 2 | N$^1$-ethyl-N$^1$-dimethyl ethane-1,2-di-amine HCl | 6 gm | 138 | 0.04343 | 10 | In house |
| 3 | Acetonitrile | 36 ml | | | 9 vol | |
| 4 | Water | 4.0 ml | | | 1 vol | |
| 5 | TEA | 5.3 gm | 101 | 0.0521 | 12 | SDFCL |

Into a clean and dried 100 ml two necked round-bottomed flask equipped with magnetic stirrer and nitrogen set up, Compound 11 (4 gm, 0.0043 mol), 35 ml 1:1 mixture of acetonitrile:water, Dimethyl 1,2-diamine (4 gm, 0.0456 mole) and TEA (5.3 gm, 0.0521 moles) were added at RT. The reaction mixture was heated at 65° C. and maintained for 6 hrs. The reaction was monitored by TLC using 60% ethyl acetate in hexane. After completion of the reaction, reaction was concentrated and quenched with 60 ml of ice cold water and the obtained precipitate was filtered and dried to yield 4 g of crude Compound 12G, which was taken as it was for next step.

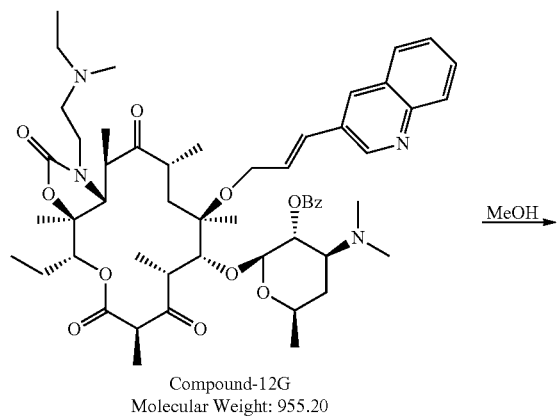

Compound-12G
Molecular Weight: 955.20

MeOH

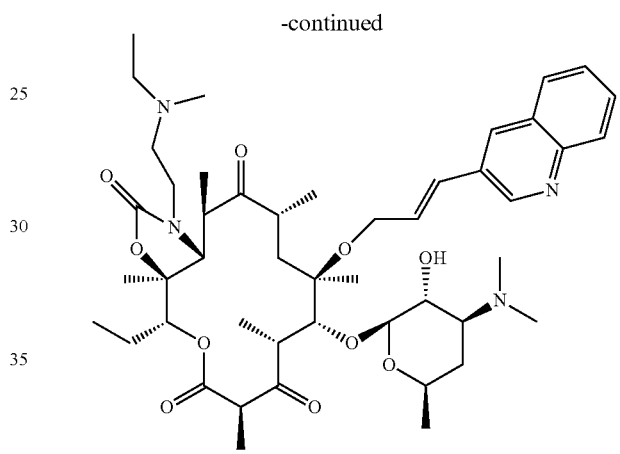

Compound-13G
Molecular Weight: 851.10

| Sl No | Raw materials | Wt (gm) | M. Wt | Moles | Eq | Source |
|---|---|---|---|---|---|---|
| 1 | Compound-12 G | 4.0 gm | 955 | 0.0041 | 1.0 | In house |
| 2 | Methanol | 40 ml | — | — | 10 vol | |

Into a clean and dried 100 ml two necked round-bottomed flask equipped with magnetic stirrer and nitrogen set up, Compound 12G (4.0 gm, 0.0044 mol) and 40 ml of methanol were added. The solution was heated at 65° C. and maintained for 4 hrs. The reaction was monitored by TLC using 10% MeOH in DCM. After completion of the reaction, reaction mass was concentrated and quenched with 40 ml of ice cold water; obtained precipitate was extracted with 2×40 ml of ethyl acetate. Combined organic layers were washed with 2×25 ml of brine solution, dried over sodium sulfate and concentrated under reduced pressure to yield 2.1 g of crude compound which was purified by prep HPLC (two times) to get the desired compound 13G of 100 mg with 90% HPLC purity (yield; 2% from Compound 11 to 13G).

1H NMR (DMSO, 400 MHz): 9.01 (s, 1H), 8.21 (s, 1H), 7.92-8.00 (m, 2H), 7.61-7.73 (m, 1H), 7.58-7.61 (m, 1H), 6.63-6.67 (d, 1H), 6.26-6.30 (m, 1H), 5.05-5.07 (m, 1H), 4.18-4.45 (m, 5H), 3.56-4.02 (m, 4H), 2.49-2.57 (m, 4H), 2.27-2.45 (m, 4H), 1.73-2.22 (m, 18H), 1.03-1.62 (m, 16H), 0.74-0.89 (m, 10H)

Example 9. Synthesis of Compound 13H

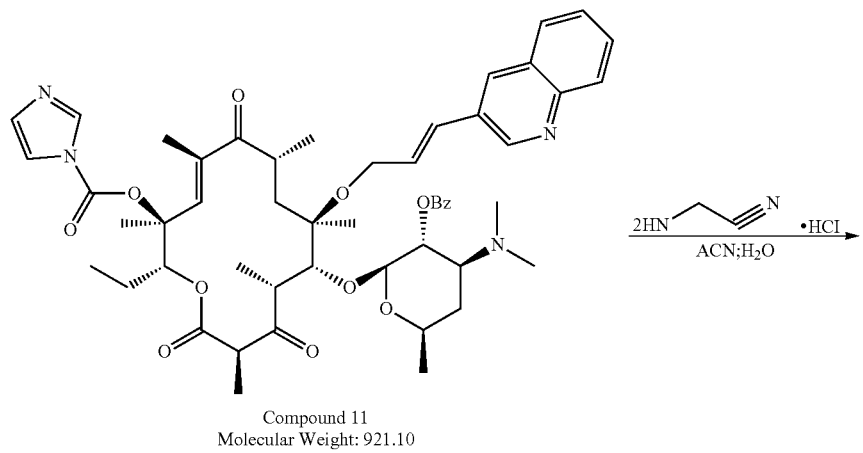

Compound 11
Molecular Weight: 921.10

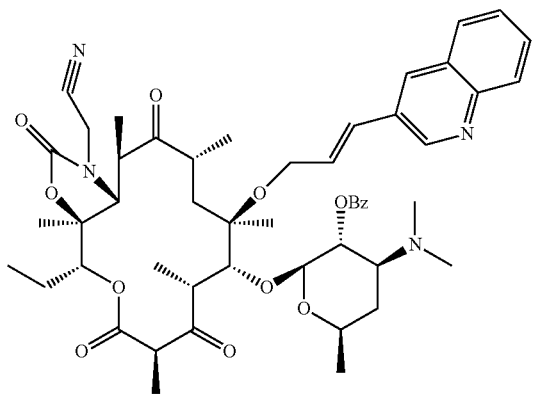

Compound 12H
Molecular Weight: 909.09

| Sl No | Raw materials | Wt (gm) | M. Wt | Moles | Eq | Source |
|---|---|---|---|---|---|---|
| 1 | Compound-11 | 4 gm | 921.10 | 0.0043 | 1.0 | In house |
| 2 | amino aceto-nitrile HCl | 6 gm | 92.53 | 0.0651 | 15 | Lancaster |
| 3 | Acetonitrile | 36 ml | | | 9 vol | Spectrochem |
| 4 | Water | 4.0 ml | | | 1 vol | |
| 5 | 1,1,3,3,tetra methyl guanidine | 7.5 gm | 115.18 | 0.06514 | 15 | Aldrich |

Into a clean and dried 100 ml two necked round-bottomed flask equipped with magnetic stirrer and nitrogen set up, Compound 11 (4 gm, 0.0043 mol), 40 ml 1:1 mixture of acetonitrile:water, 1,1,3,3, tetra methyl guanidine (7.5 gm, 0.06514 mol) and amino acetonitrile hydrochloride (6 gm, 0.0651 mole) were added at RT. The reaction mixture was heated at 65° C. and maintained for 6 hrs. The reaction was monitored by TLC using 60% ethyl acetate in hexane. After completion of the reaction, reaction mass was concentrated under reduced pressure and quenched with 60 ml of ice cold water and the obtained precipitate was filtered and dried to yield 4 g of crude Compound 12H, which was taken as it was for next step.

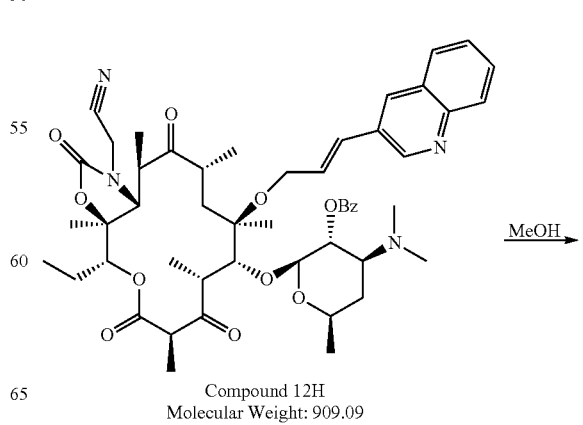

Compound 12H
Molecular Weight: 909.09

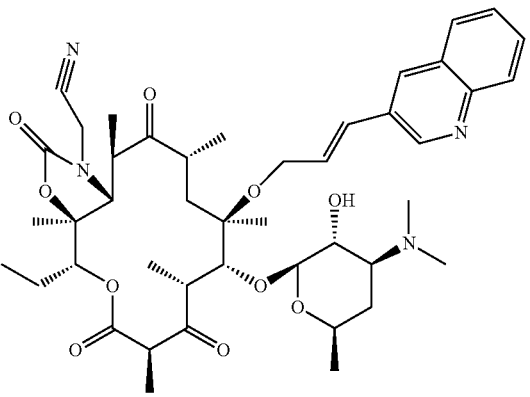

Compound13 H
Molecular Weight: 804.98

| Sl No | Raw materials | Wt (gm) | M. Wt | Moles | Eq | Source |
|---|---|---|---|---|---|---|
| 1 | Compound-12 H | 4.0 gm | 909.09 | 0.0044 | 1.0 | In house |
| 2 | Methanol | 40 ml | — | — | 10 vol | |

Into a clean and dried 100 ml two necked round-bottomed flask equipped with magnetic stirrer and nitrogen set up, Compound 12H (4.0 gm, 0.0044 mol) and 40 ml of methanol were added. The reaction mixture was heated at 65° C. and maintained for 4 hrs. The reaction was monitored by TLC using 10% MeOH in DCM. After completion of the reaction, reaction mass was concentrated under reduced pressure and quenched with 40 ml of ice cold water; obtained precipitate was extracted with 2×40 ml of ethyl acetate. Combined organic layers were washed with 2×25 ml of solution, dried over sodium sulfate and concentrated under reduced pressure to yield 2.5 g of crude compound which was purified by prep HPLC (two times) to get the desired Compound 13H of 20 mg with 89.3% HPLC purity (yield; 2% from Compound 11 to 13H).

1H NMR (DMSO, 400 MHz): 9.04-9.05 (d, 1H, J=4), 8.29 (s, 1H), 7.92-7.8.01 (m, 2H), 7.71-7.75 (m, 1H), 7.59-7.63 (m, 1H), 6.66-6.70 (m, 1H), 6.13-6.21 (m, 1H), 4.72-4.80 (m, 1H), 4.10-4.31 (m, 5H), 3.64-3.83 (m, 3H), 2.98-3.15 (m, 2H), 1.98-2.32 (m, 6H), 1.54-1.60 (m, 6H), 1.34-1.43 (m, 6H), 1.15-1.29 (m, 10H), 0.95-1.10 (m, 7H), 0.77-0.85 (m, 6H)

Example 10. Synthesis of Compound 13I

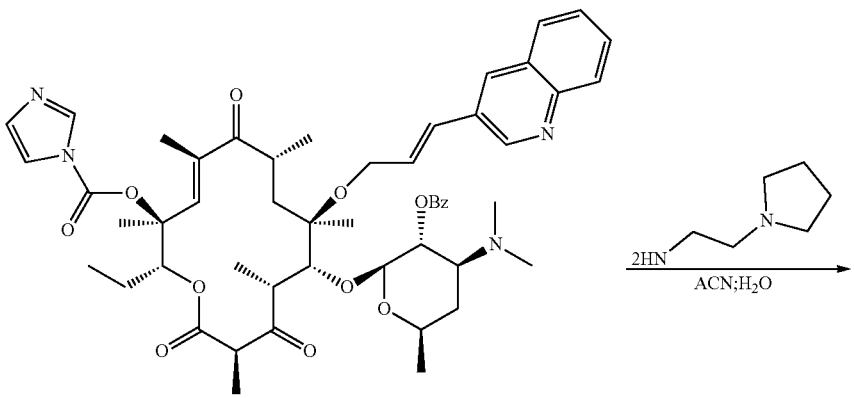

Compound 11
Molecular Weight: 921.10

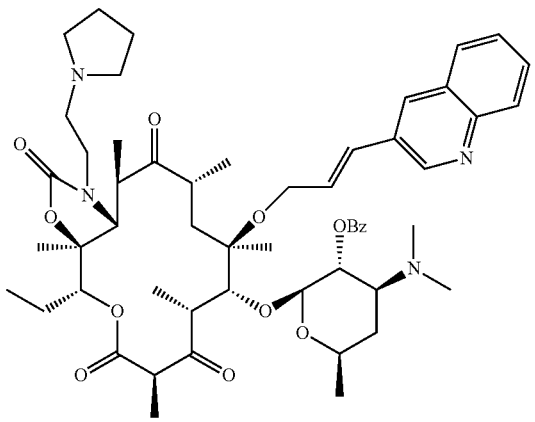

Compound 12I
Molecular Weight: 967.21

| Sl No | Raw materials | Quantity | M. Wt | Mole | Eq | Source |
|---|---|---|---|---|---|---|
| 1 | Compound-11 | 3 g | 921.10 | 0.00325 | 1.0 | In house |
| 2 | 2-(pyrrolidin-1-yl)ethan-1-amine | 3.7 g | 114.12 | 0.0325 | 10 | Chemlabs |
| 3 | Acetonitrile | 27 mL | | | 9 vol | Merck |
| 4 | Water | 3 mL | | | 1 vol | |

To a clean and dried 100 mL two necked RBF equipped with magnetic stirrer and nitrogen bubbler, was added Compound 11 (3 g, 0.0032 mol), 30 mL 9:1 mixture of acetonitrile:water and 2-(pyrrolidin-1-yl)ethan-1-amine (3.7 g, 0.032 mol) at RT. The reaction mixture was maintained for 6 h at 65° C. and it was monitored by TLC using 10% Methanol in DCM. After completion of the reaction, the reaction mass was concentrated and quenched with 60 ml of ice cold water. The precipitate obtained was filtered and dried to get 4 g of crude compound, which was taken as such for next stage.

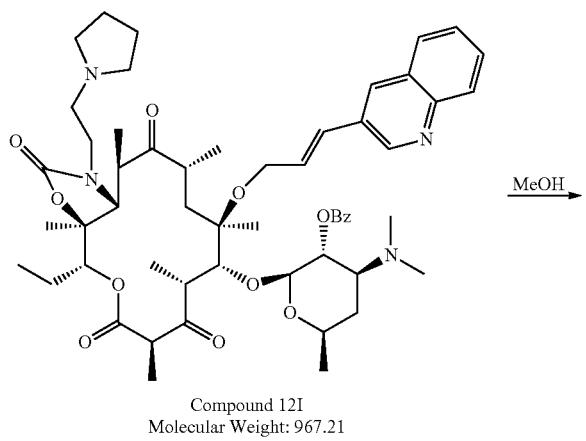

Compound 12I
Molecular Weight: 967.21

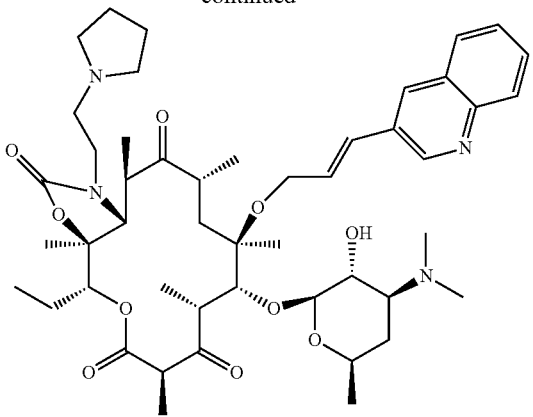

Compound 13I
Molecular Weight: 863.11

| Sl No | Raw materials | Quantity | M. Wt | Mole | Eq | Source |
|---|---|---|---|---|---|---|
| 1 | Compound-12 I | 4.0 g | 967.21 | 0.0041 | 1.0 | In house |
| 2 | Methanol | 40 mL | — | — | 10 vol | |

To a clean and dried 100 ml two necked RBF equipped with magnetic stirrer and nitrogen bubbler, added Compound 12I (4.0 gm, 0.0041 mol), 40 ml of methanol. The reaction mixture was maintained for 4 hrs at 65° C. and monitored by TLC using 10% MeOH in DCM. Upon completion of the reaction. The reaction mass was concentrated and quenched with 40 mL of ice cold water; obtained product was extracted with 2×40 ml of ethyl acetate. Combined organic layer was washed with 2×25 mL of sat. brine solution, dried over sodium sulphate and concentrated under reduced pressure to get 2.5 g of crude compound which was purified by prep HPLC (twice) to get the desired compound of 300 mg with 95.8% HPLC purity.

$^1$H NMR (DMSO, 300 MHz): 9.05 (s, 1H, J=3 Hz), 8.22 (s, 1H), 7.93-8.0 (m, 2H),7.69-7.74 (m, 1H), 7.60-7.62 (m, 1H), 6.63-6.69 (d, 1H), 6.30-6.37 (m, 1H), 5.13-5.16 (m, 1H), 4.17-4.37 (m, 4H), 3.77-3.85 (m, 2H), 3.53-3.60 (m, 4H), 3.08-3.35 (m, 2H), 2.65-2.72 (m, 3H), 2.20-2.30 (m, 10H), 1.49-1.98 (m, 6H), 1.23-138 (m, 10H), 1.15-1.21 (m, 8H), 0.96-1.13 (m, 8H), 0.78-0.85 (m, 4H)

Example 11. Synthesis of Compound 13J

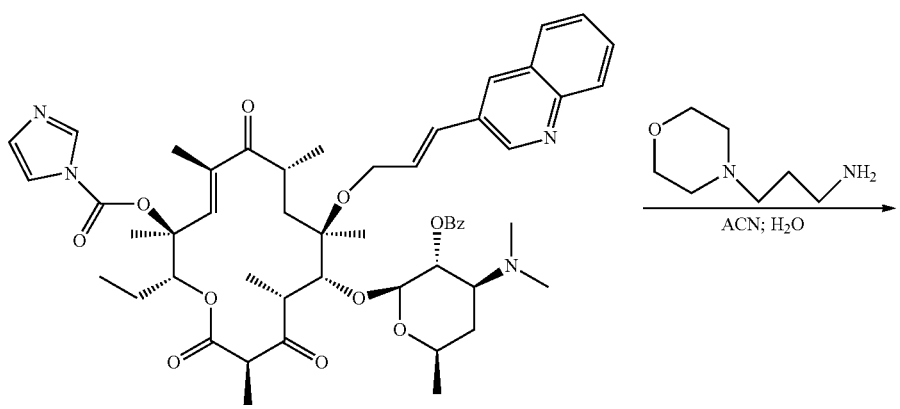

Compound 11
Molecular Weight: 921.10

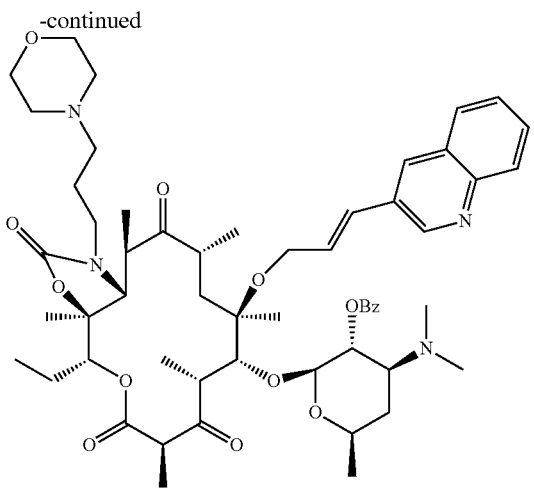

Compound-12 J
Molecular Weight: 997.24

| Sl No | Raw materials | Quantity | M. Wt | Mole | Eq | Source |
|---|---|---|---|---|---|---|
| 1 | Compound-11 | 3 g | 921.10 | 0.0032 | 1.0 | In house |
| 2 | 3-morpholinopropan-1-amine | 4.6 g | 144 | 0.0325 | 10 | Aldrich |
| 3 | Acetonitrile | 27 mL | | | 9 vol | Spectrochem |
| 4 | Water | 3 mL | | | 1 vol | |

To a clean and dried 100 mL two necked RBF equipped with magnetic stirrer and nitrogen bubbler, was added Compound 11 (3 g, 0.0032 mol), 30 mL 9:1 mixture of acetonitrile:water and 3-morpholinopropan-1-amine (4.6 g, 0.0325 mol) at RT. The reaction mixture was maintained for 6 h at 65° C. and was monitored by TLC using 10% Methanol in DCM. After completion of the reaction, the reaction mass was concentrated and quenched with 60 mL of ice cold water and the obtained precipitate was filtered and dried to get 4 g of crude compound, which was taken as such for next stage.

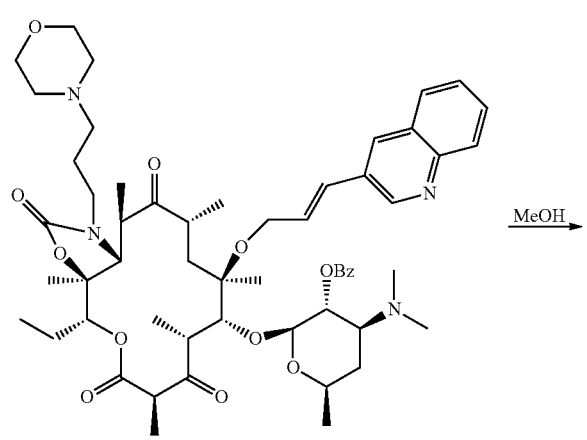

Compound-12 J
Molecular Weight: 997.24

MeOH →

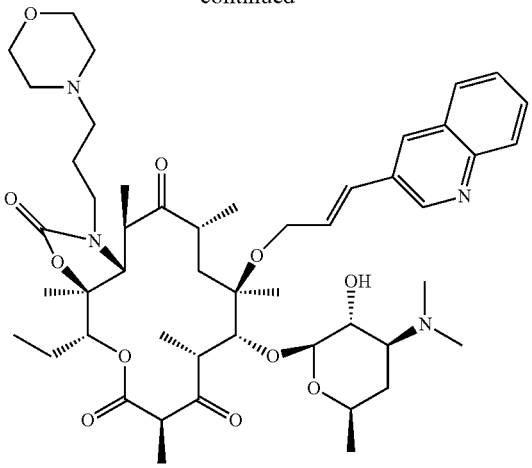

Compound-13 J
Molecular Weight: 893.13

| Sl No | Raw materials | Quantity | M. Wt | Mole | Eq | Source |
|---|---|---|---|---|---|---|
| 1 | Compound-12 J | 4.0 g | 997 | 0.004 | 1.0 | In house |
| 2 | Methanol | 40 mL | — | — | 10 vol | |

To a clean and dried 100 ml two necked RBF equipped with magnetic stirrer and nitrogen set up, was added Compound 12J (4.0 g, 0.004 mol), 40 mL of methanol. The reaction mixture was maintained for 4 hrs at 65° C. and monitored by TLC using 10% MeOH in DCM. After completion of the reaction, it was concentrated and quenched with 40 ml of ice cold water; obtained product was extracted with 2×40 mL of ethyl acetate. Combined organic layer was washed with 2×25 mL of sat. brine solution, dried over sodium sulphate and concentrated under reduced pressure to get 2.5 g of crude compound. The crude was purified by prep HPLC (twice) to get the desired compound (120 mg with 89.3% HPLC purity).

$^1$H NMR (DMSO, 300 MHz): 9.05 (s, 1H, J=1.8 Hz), 8.23 (s, 1H), 7.92-8.0 (m, 2H), 7.69-7.72 (m, 1H), 7.60-7.63 (m,

1H), 6.64-6.69 (d, 1H), 6.30-6.37 (m, 1H), 5.13-5.16 (m, 1H), 4.16-4.36 (m, 4H), 3.41-3.60 (m, 4H), 3.07-3.34 (m, 4H), 2.08-2.7 (m, 9H), 1.81-1.96 (m, 8H), 1.49-1.61 (m, 8H), 1.33-1.38 (m, 6H), 1.08-1.23 (m, 8H), 0.93-1.07 (m, 7H), 0.80-0.85 (m, 5H)

Example 12. Synthesis of Compound 13K

To a clean and dried 100 ml two necked RBF equipped with magnetic stirrer and nitrogen bubbler, was added Compound 11 (3 g, 0.003256 mol), 30 mL 9:1 mixture of acetonitrile:water and 2-(4-methylpiperazin-1-yl)ethan-1-amine (4.6 g, 0.03257 mole) at RT. The reaction mixture was maintained for 6 h at 65° C. and it was monitored by TLC

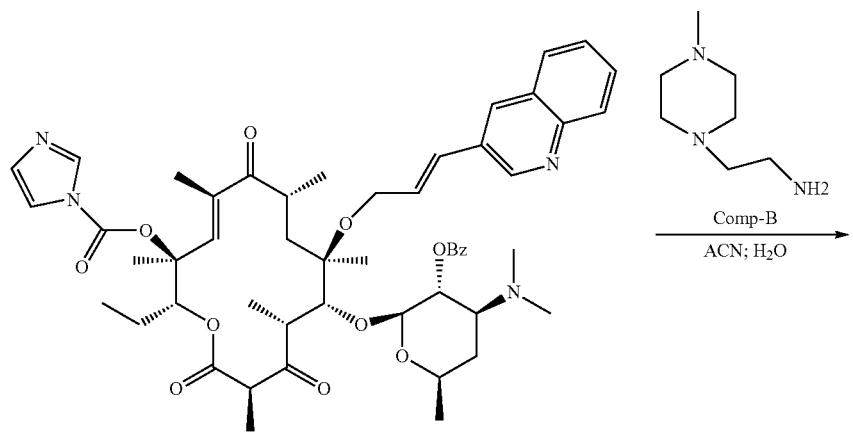

Compound 11
Molecular Weight: 921.10

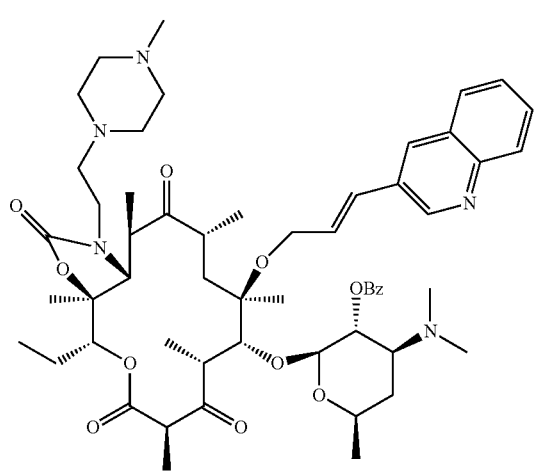

Compound-12 K
Molecular Weight: 996.26

| Sl No | Raw materials | Quantity | M. Wt | Mole | Eq | Source |
|---|---|---|---|---|---|---|
| 1 | Compound-11 | 3 g | 921.10 | 0.0032 | 1.0 | In house |
| 2 | 2-(4-methylpiperazin-1-yl)ethan-1-amine | 4.6 g | 143 | 0.0325 | 10 | Aldrich |
| 3 | Acetonitrile | 27 mL | | | 9 vol | Spectrochem |
| 4 | Water | 3 mL | | | 1 vol | | using 10% Methanol in DCM. After completion of the reaction, it was concentrated and quenched with 60 mL of ice cold water and the obtained precipitate was filtered and dried to get 4 g of crude compound, which was taken as such for next stage.

¹H NMR (DMSO, 300 MHz): 9.05 (s, 1H), 8.21 (s, 1H), 7.93-8.0 (m, 2H),7.69-7.74 (m, 1H), 7.60-7.63 (m, 1H), 6.62-6.68 (d, 1H), 6.30-6.37 (m, 1H), 5.14 (m, 1H), 4.17-4.35 (m, 4H), 3.45-3.75 (m, 10H), 3.07-3.34 (m, 3H), 2.20-2.26 (m, 7H), 1.76-2.07 (m, 8H), 1.49-1.54 (m, 6H), 1.16-1.49 (m, 13H), 0.93-1.15 (m, 7H), 0.82-0.87 (m, 4H)

Example 13. Synthesis of Compound 13L

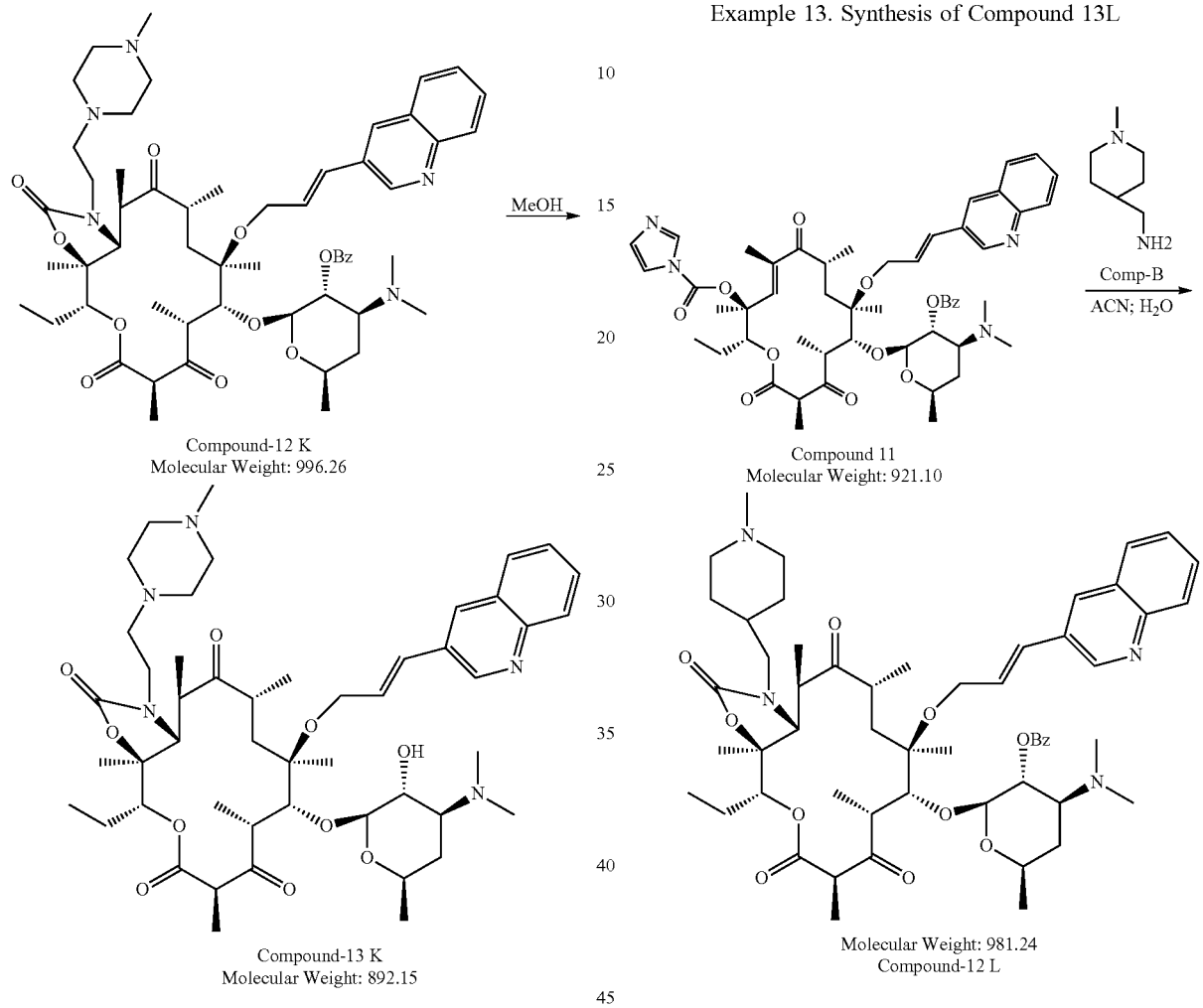

| Sl No | Raw materials | Quantity | M. Wt | Mole | Eq | Source |
|---|---|---|---|---|---|---|
| 1 | Compound-12 K | 4.0 g | 996 | 0.004 | 1.0 | In house |
| 2 | Methanol | 40 mL | — | — | 10 vol | |

To a clean and dried 100 mL two necked RBF equipped with magnetic stirrer and nitrogen bubbler, added Compound 12K (4.0 g, 0.004 mol), 40 ml of methanol. The reaction mixture was maintained for 4 h at 65° C. and monitored by TLC using 10% MeOH in DCM. Upon completion of the reaction, it was concentrated and quenched with 40 mL of ice cold water; obtained product was extracted with 2×40 ml of ethyl acetate. Combined organic layer was washed with 2×25 mL of sat. brine solution, dried over sodium sulphate and concentrated under reduced pressure to get 2.5 g of crude compound. The crude was purified by prep HPLC (twice) to get the desired compound (60 mg with 95% HPLC purity).

| Sl No | Raw materials | Quantity | M. Wt | Mole | Eq | Source |
|---|---|---|---|---|---|---|
| 1 | Compound-11 | 3 g | 921.10 | 0.0032 | 1.0 | In house |
| 2 | (1-methyl-piperidin-4-yl)-methanamine | 4.1 g | 128 | 0.0325 | 10 | Aldrich |
| 3 | Acetonitrile | 27 mL | | | 9 vol | Spectrochem |
| 4 | Water | 3 mL | | | 1 vol | |

To a clean and dried 100 mL two necked RBF equipped with magnetic stirrer and nitrogen bubbler, added Compound 11 (3 g, 0.0032 mol), 30 mL 9:1 mixture of acetonitrile:water and (1-methylpiperidin-4-yl)methanamine (4.1 g, 0.0325 mol) at RT. The reaction mixture was maintained for 6 h at 65° C. and it was monitored by TLC using 10% methanol in DCM. Upon completion of the reaction, reaction mass was concentrated and quenched with 60 mL of ice cold water. The obtained precipitate was filtered and dried to get 3 g of crude compound, which was taken as such for next stage.

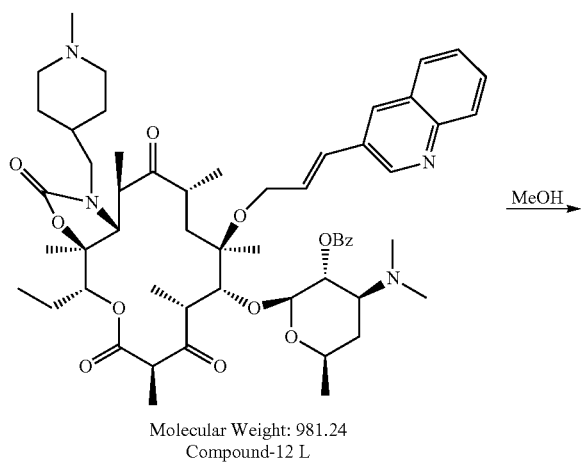

Molecular Weight: 981.24
Compound-12 L

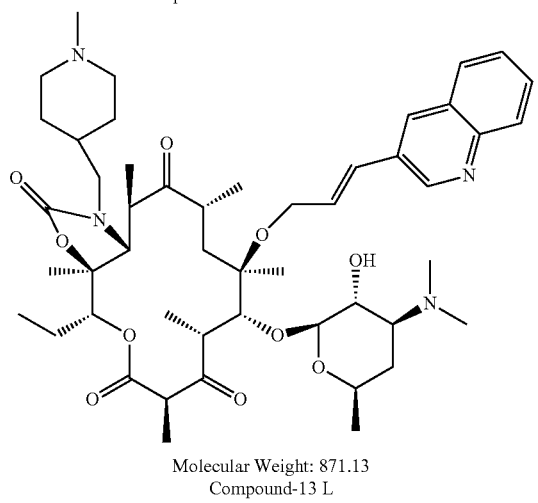

Molecular Weight: 871.13
Compound-13 L

| Sl No | Raw materials | Quantity | M. Wt | Mole | Eq | Source |
|---|---|---|---|---|---|---|
| 1 | Compound-12 L | 3.0 g | 981 | 0.003 | 1.0 | In house |
| 2 | Methanol | 40 mL | — | — | 10 vol | |

To a clean and dried 100 mL two necked RBF equipped with magnetic stirrer and nitrogen bubbler, was added Compound 12L (3.0 g, 0.004 mol), 40 ml of methanol. The reaction mixture was stirred for 4 h at 65° C. and monitored by TLC using 10% MeOH in DCM. Upon completion of the reaction, the reaction mass was concentrated and quenched with 40 mL of ice cold water; obtained product was extracted with 2×40 mL of ethyl acetate. The combined organic layer was washed with 2×25 mL of sat. brine solution, dried over sodium sulphate and concentrated under reduced pressure to get 2.5 g of crude compound. The crude was purified by preparative HPLC (twice) to get the desired compound (170 mg with 95% HPLC purity).

$^1$H NMR (DMSO, 400 MHz): 9.05 (d, 1H, J=2 Hz), 8.21 (d, 1H, J=1.6 Hz), 7.92-8.0 (m, 2H),7.69-7.73 (m, 1H), 7.58-7.62 (m, 1H), 6.67-6.71 (d, 1H), 6.30-6.37 (m, 1H), 4.97-4.99 (m, 1H), 4.16-4.35 (m, 4H), 3.76-3.84 (m, 2H), 3.67 (s, 1H), 2.88-3.41 (m, 5H), 2.58-2.67 (m, 2H), 2.17-2.32 (m, 6H), 1.77-1.87 (m, 5H), 1.46-1.70 (m, 9H), 1.06-1.44 (m, 19H), 0.81-0.99 (m, 7H)

Example 14. Synthesis of Compound 13M

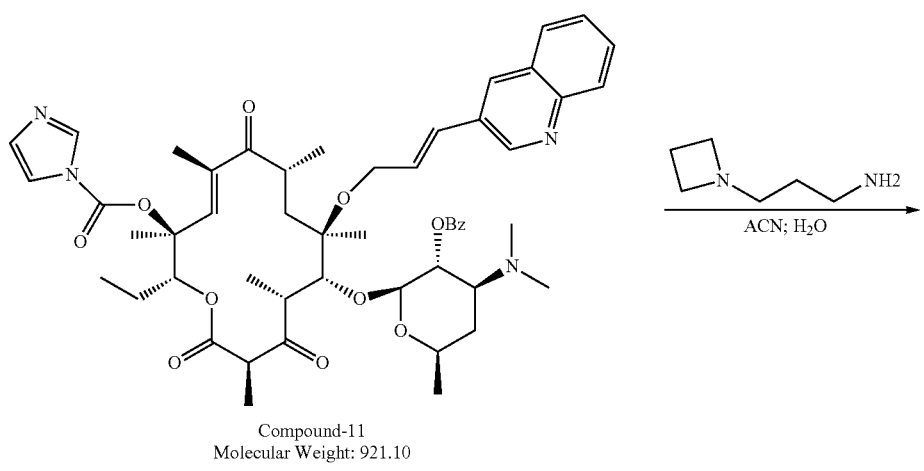

Compound-11
Molecular Weight: 921.10

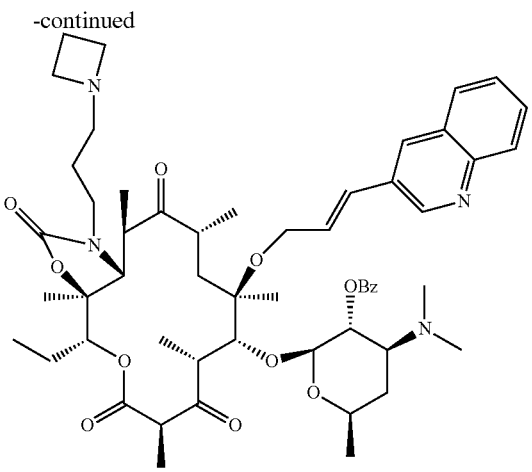

Compound-12 M
Molecular Weight: 967.21

| Sl No | Raw materials | Quantity | M. Wt | Mole | Eq | Source |
|---|---|---|---|---|---|---|
| 1 | Compound-11 | 5 g | 921.10 | 0.0054 | 1.0 | In house |
| 2 | 3-(azetidin-1-yl)propan-1-amine | 1.86 g | 114.19 | 0.0162 | 3 | Bepharm Ltd |
| 3 | Acetonitrile | 45 mL | | | 9 vol | Spectrochem |
| 4 | Water | 5 mL | | | 1 vol | |

To a clean and dried 100 mL two necked RBF equipped with magnetic stirrer and nitrogen bu, added Compound 11 (5 g, 0.0054 mol), 50 mL of 9:1 of ACN; water mixture, and 3-(azetidin-1-yl)propan-1-amine (1.86 g, 0.0162 mol) at RT. The reaction mixture was stirred for 4 h at 65° C. and it was monitored by TLC using ethyl acetate. After completion of the reaction, it was concentrated and quenched with 100 mL of ice cold water at 10-15° C. and the precipitated solid filtered and dried to get 5 g of crude compound, which was taken as such for next step.

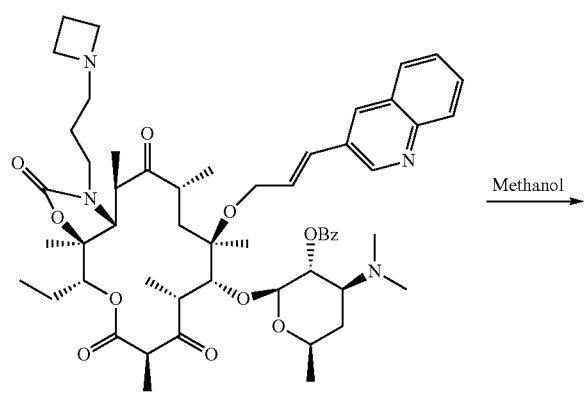

Compound-12 M
Molecular Weight: 967.21

→ Methanol

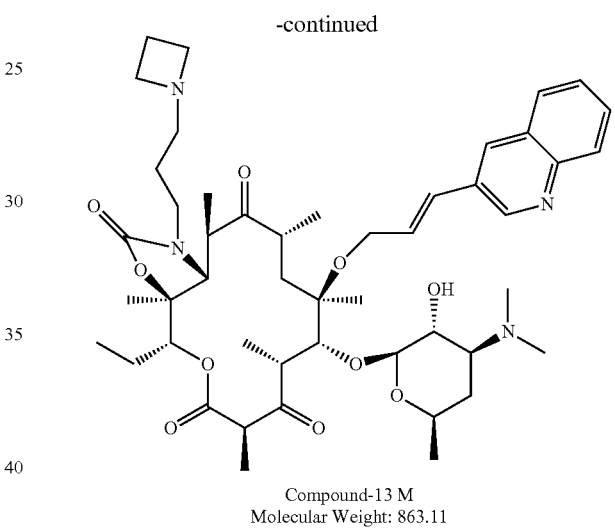

Compound-13 M
Molecular Weight: 863.11

| Sl No | Raw materials | Quantity | M. Wt | Mole | Eq | Source |
|---|---|---|---|---|---|---|
| 1 | Compound-12 M | 5 g | 967 | 0.0052 | 1.0 | In house |
| 2 | Methanol | 50 mL | — | — | 10 vol | |

To a clean and dried 100 mL two necked RBF equipped with magnetic stirrer and nitrogen bubbler, added Compound 12M (5 g, 0.0052 mol), 50 mL of methanol and the reaction mixture was maintained for 4 h at 65° C. and was monitored by TLC using 10% MeOH; DCM. Upon completion of the reaction, the reaction mass was concentrated and quenched with 50 ml of ice cold water, extracted with 2×40 mL of ethyl acetate. The combined organic layer was washed with 2×25 mL sat. brine solution, dried over sodium sulphate and concentrated to get 3.2 g of crude. The crude compound was purified by preparative HPLC purification (twice) to get 100 mg of the desired compound.

$^1$H NMR (DMSO, 400 MHz): 9.04 (d, 1H, J=2 Hz), 8.23-8.24 (d, 1H, J=4 Hz), 7.94-8.01 (m, 2H), 7.69-7.74 (m, 1H), 7.58-7.62 (m, 1H), 6.65-6.69 (d, 1H), 6.26-6.30 (m,

1H), 4.85-4.91 (m, 1H), 4.17-4.35 (m, 4H), 3.76-3.86 (m, 2H), 3.60 (s, 1H), 3.41-3.43 (m, 1H), 2.91-3.33 (m, 6H), 2.49-2.66 (m, 4H), 2.08-2.22 (m, 5H), 1.48-1.90 (m, 12H), 1.09-1.37 (m, 19H), 0.80-0.93 (m, 7H)

Example 15. Synthesis of Compound 13N

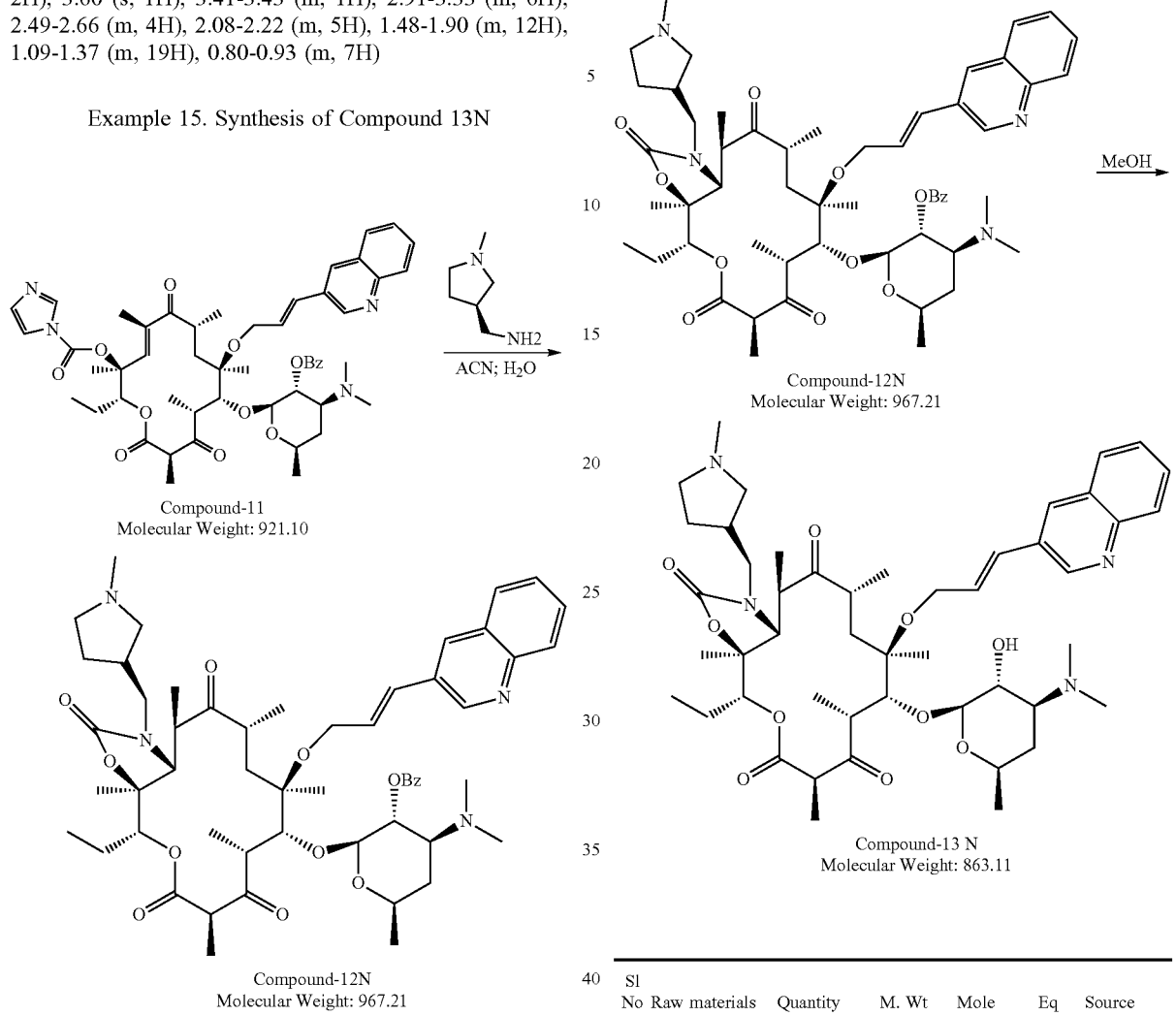

| Sl No | Raw materials | Quantity | M. Wt | Mole | Eq | Source |
|---|---|---|---|---|---|---|
| 1 | Compound-11 | 5 gm | 921.1 | 0.0054 | 1.0 | In house |
| 2 | (R)-(1-methylpyrrolidin-3-yl)methanamine | 1.85 gm | 114 | 0.0162 | 3 | Be pharm Ltd |
| 3 | Acetonitrile | 45 ml | | | 9 vol | Merck |
| 4 | water | 5 ml | | | 1 vol | |

To a clean and dried 100 mL two necked RBF equipped with magnetic stirrer and nitrogen bubbler, was added Compound 11 (5 g, 0.0054 mol), 50 ml of 9:1 of ACN; water mixture, and (R)-(1-methylpyrrolidin-3-yl)methanamine (1.86 g, 0.0162 mol) at RT. The reaction mixture was stirred for 4 hrs at 65° C. and was monitored by TLC using ethyl acetate. Upon completion of the reaction, the reaction mixture was concentrated and quenched with 100 mL of ice cold water. The precipitated solid was filtered and dried to get 5 g crude compound, which was taken as such for next step.

| Sl No | Raw materials | Quantity | M. Wt | Mole | Eq | Source |
|---|---|---|---|---|---|---|
| 1 | Compound-12N | 5 g | 967 | 0.0052 | 1.0 | In house |
| 2 | Methanol | 50 mL | — | — | 10 vol | |

To a clean and dried 100 mL two necked RBF equipped with magnetic stirrer and nitrogen bubbler, added Compound 12N (5 g, 0.0052 mol), 40 mL of methanol and the reaction mixture was stirred for 4 h at 65° C. and was monitored by TLC using 10% MeOH; DCM. Upon completion of the reaction, the reaction mass was concentrated and quenched with 50 mL of ice cold water, extracted with 2×40 mL of ethyl acetate. The combined organic layer was washed with 2×25 ml sat. brine solution, dried over sodium sulphate and concentrated to get 3.2 g of crude compound. The crude compound was purified by preparative HPLC (twice) to get 130 mg of the desired compound (91% purity by HPLC).

$^1$H NMR (DMSO, 400 MHz): 9.06 (d, 1H, J=2 Hz), 8.22-8.23 (d, 1H, J=4 Hz), 7.93-8.00 (m, 2H), 7.69-7.73 (m, 1H), 7.58-7.62 (m, 1H), 6.66-6.71 (d, 1H), 6.30-6.35 (m, 1H), 4.86-4.91 (m, 1H), 4.17-4.38 (m, 4H), 3.76-3.85 (m, 2H), 3.67 (s, 1H), 3.07-3.34 (m, 5H), 2.67-2.69 (m, 1H), 2.09-2.50 (m, 10H), 1.37-1.88 (m, 18H), 1.05-1.25 (m, 13H), 0.80-0.95 (m, 7H)

Example 16. Synthesis of Compound 13P

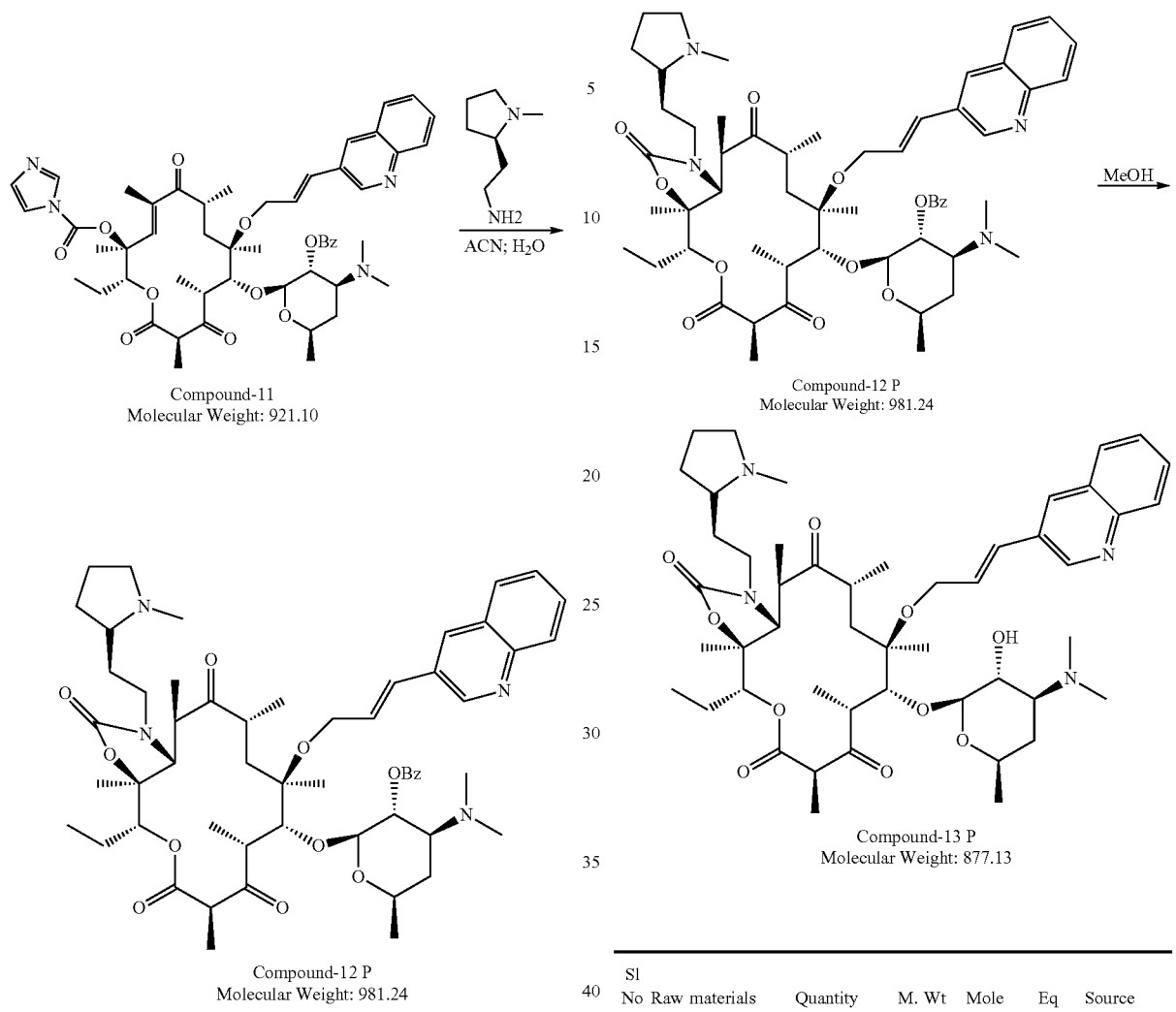

| Sl No | Raw materials | Quantity | M. Wt | Mole | Eq | Source |
|---|---|---|---|---|---|---|
| 1 | Compound-11 | 5 g | 921.10 | 0.0054 | 1.0 | In house |
| 2 | (R)-2-(1-ethylpyrrolidin-2-yl)ethan-1-amine | 2.08 g | 128 | 0.0162 | 3 | Be pharm Ltd. |
| 3 | Acetonitrile | 45 mL | | | 9 vol | Merck |
| 4 | Water | 5 mL | | | 1 vol | |

To a clean and dried 100 mL two necked RBF equipped with magnetic stirrer and nitrogen bubbler, added Compound 11 (5 g, 0.0054 mol), 50 mL of 9:1 of ACN; water mixture, and (R)-2-(1-ethylpyrrolidin-2-yl)ethan-1-amine (2.08 g, 0.0162 mol) at RT. The reaction mixture was stirred for 4 h at 65° C. and was monitored by TLC using 100% ethylacetate. Upon completion of the reaction, the reaction mass was concentrated and quenched with 100 mL of ice cold water. The precipitated solid was filtered and dried to get 5 g crude compound, which was taken as such for next step.

| Sl No | Raw materials | Quantity | M. Wt | Mole | Eq | Source |
|---|---|---|---|---|---|---|
| 1 | Compound-12 P | 5 g | 981 | 0.005 | 1.0 | In house |
| 2 | Methanol | 50 mL | — | — | 10 vol | |

To a clean and dried 100 mL two necked RBF equipped with magnetic stirrer and nitrogen bubbler, added Compound 12 P (5 g, 0.005 mol), 40 mL of methanol and the reaction mixture was stirred for 4 h at 65° C. and was monitored by TLC using 10% MeOH; DCM. Upon completion of the reaction, the reaction mass was concentrated and quenched with 50 mL of ice cold water, extracted with 2×40 mL of ethyl acetate. The combined organic layer was washed with 2×25 mL sat. brine solution, dried over sodium sulphate and concentrated to get 3.2 g of crude compound. The crude compound was purified by preparative HPLC (twice) to get 140 mg of the desired compound (92% HPLC purity).

$^1$H NMR (DMSO, 400 MHz): 9.0 (d, 1H, J=4 Hz), 8.21 (s, 1H), 7.92-8.01 (m, 2H), 7.69-7.73 (t, 1H, J=8 Hz), 7.58-7.62 (m, 1H), 6.65-6.69 (m, 1H), 6.23-6.27 (m, 1H), 4.86-4.88 (m, 1H), 4.17-4.36 (m, 4H), 3.79-3.82 (m, 2H), 3.63 (s, 1H), 3.07-3.30 (m, 4H), 2.43-2.67 (m, 3H), 1.98-2.18 (m, 7H), 1.7-1.94 (m, 6H), 1.50-1.64 (m, 10H), 1.29-1.38 (m, 8H), 1.03-1.23 (m, 10H), 0.94-1.02 (m, 7H), 0.80-0.84 (m, 3H)

Example 17. Synthesis of Compound 13Q

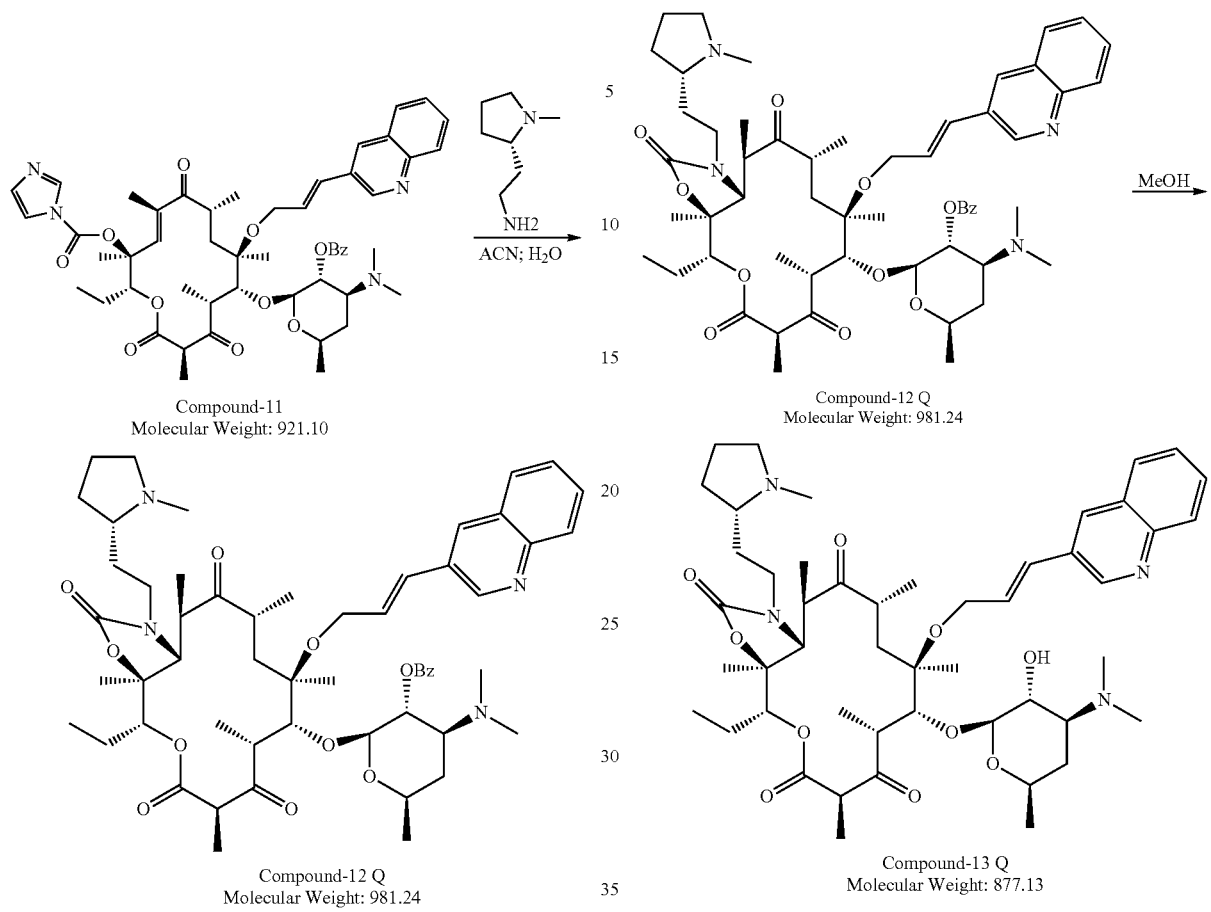

| Sl No | Raw materials | Quantity | M. Wt | Mole | Eq | Source |
|---|---|---|---|---|---|---|
| 1 | Compound-11 | 5 g | 921.10 | 0.0054 | 1.0 | In house |
| 2 | (S)-2-(1-ethylpyrrolidin-2-yl)ethan-1-amine | 2.08 g | 128 | 0.0162 | 3 | Be pharm Ltd. |
| 3 | Acetonitrile | 25 mL | | | 5 vol | Merck |
| 4 | Water | 2 5 mL | | | 5 vol | |
| 5 | 1,1,3,3 tetra methyl guanidine | 3.12 g | 115.18 | 0.0271 | 5 | Aldrich |

To a clean and dried 100 mL two necked RBF equipped with magnetic stirrer and nitrogen bubbler, added Compound 11 (5 g, 0.0054 mol), 50 mL of 5:5 of ACN; water mixture, and 1,1,3,3 tetra methyl guanidine (3.12 g, 0.027 mol) followed by (S)-2-(1-ethylpyrrolidin-2-yl)ethan-1-amine (2.08 g, 0.0162 mol) at RT. The reaction mixture was stirred for 4 h at 65° C. and was monitored by TLC using 100% ethyl acetate. After completion of the reaction, the reaction mass was concentrated and quenched with 100 ml of ice cold water. The precipitated solid was filtered and dried to get 5 g crude compound, which was taken as such for next step (LC-MS).

| Sl No | Raw materials | Quantity | M. Wt | Mole | Eq | Source |
|---|---|---|---|---|---|---|
| 1 | Compound-12 Q | 5 g | 981 | 0.005 | 1.0 | In house |
| 2 | Methanol | 50 mL | — | — | 10 vol | |

In to a clean and dried 100 mL two necked RBF equipped with magnetic stirrer and nitrogen bubbler, added Compound 12 Q (5 g, 0.005 mol), 40 mL of methanol and the reaction mixture was maintained for 4 h at 65° C. and was monitored by TLC using 10% MeOH; DCM. Upon completion of the reaction, the reaction mass was concentrated and quenched with 50 mL of ice cold water, extracted with 2×40 mL of ethyl acetate. The combined organic layer was washed with 2×25 mL sat. brine solution, dried over sodium sulphate and concentrated to get 3.2 g of crude compound. The crude compound was purified by preparative HPLC (twice) to get 400 mg of the desired compound (93% HPLC purity).

$^1$H NMR (DMSO, 400 MHz): 9.0 (d, 1H, J=2 Hz), 8.21 (d, 1H, J=1 Hz), 7.92-8 (m, 2H),7.73-7.7 (m, 1H),7.58-7.62 (t, 1H, J=8 Hz), 6.64-6.68 (m, 1H), 6.26-6.3 (m, 1H),4.86-4.88 (m, 1H), 4.17-4.36 (m, 4H), 3.78-3.83 (m, 2H), 3.63 (s, 1H), 3.07-3.30 (m, 4H), 2.43-2.67 (m, 3H), 1.98-2.18 (m, 7H), 1.7-1.94 (m, 6H), 1.50-1.64 (m, 10H), 1.30-1.37 (m, 8H), 1.15-1.23 (m, 10H), 0.90-1.17 (m, 7H), 0.81-0.85 (m, 3H)

Example 17. Protocols for Determining Minimum Inhibitory Concentration (MIC) of Test Compounds Against *Streptococcus Pneumoniae* Strains

| Test organisms | |
|---|---|
| *S. pneumoniae* | AUCC479, macrolide & penicillin sensitive<br>AUCC483, macrolide resistant & penicillin sensitive<br>AUCC488, AUCC489; macrolide & penicillin resistant |
| *S. pneumoniae* | CLSI QC strain, ATCC 49619 |

Inoculum Preparation

The test strains are revived from frozen stock on blood agar plates and incubated at 35±2° C. for 18-20 hours in 5% $CO_2$. Colonies are directly suspended from an overnight grown agar culture in CAMHB/saline and optical density adjusted to 0.5 McFarland turbidity standard ($1\text{-}2\times10^8$ cfu/mL). Adjusted cultures are further diluted 1:100 using CAMHB such that after inoculation each well finally contains ~$5\times10^5$ cfu/mL. For broth dilution testing of *Streptococcus* species, CAMHB is supplemented with 2.5-5% v/v LHB. Colony counts of inoculum suspension is estimated by ten-fold serial dilutions and plating each dilution on agar plate. After incubation, the plates are observed for growth and microbial counts determined.

Test Compounds and Reference Antibiotic

Compounds are weighed and dissolved in water/DMSO/other solvent to yield 1 mg/mL stock solution. Serial two-fold dilutions of the test compounds and reference antibiotics are prepared. 50 µL of the diluted drug solutions are dispensed in wells of microtiter trays (96 well).

Erythromycin concentration range tested: 64-0.125 µg/mL

Solithromycin concentration range tested: 2-0.004 µg/mL

Test compounds concentration range tested: 4-0.008 µg/mL

Inoculation and Incubation

To each of the wells of the microtiter tray, 50 µL of the diluted organism are inoculated to obtain a final inoculum density of ~$5\times10^5$ cfu/mL. Broth control, compound control and organism control wells are set up. Microtitre trays are incubated at 35±2° C. for 20-24 hours in an ambient air incubator.

Experimental Controls

Broth control/no growth control: CAMHB supplemented with 2.5-5% v/v LHB

Organism control/growth control: Organism suspension in CAMHB supplemented with 2.5-5% v/v LHB Compound control: Compound solution diluted in CAMHB supplemented with 2.5-5% v/v LHB Standard quality control strain: *S. pneumoniae* ATCC 49619

Reference antibiotics and comparative compound: Erythromycin, solithromycin (a potent CYP3A inhibitor), clindamycin, ketoconazole (a potent CYP3A inhibitor), and Compound 13F MIC testing are done in duplicates MIC End Point MIC is defined as the lowest concentration of an antimicrobial agent that prevents visible growth of a microorganism in broth dilution susceptibility test.

After incubation period, growth of organism in the wells are detected by unaided eye facilitated by a viewing device. The amount of growth in the drug-containing wells are compared with the amount of growth in the organism-control wells. The lowest concentration of an antimicrobial agent that completely inhibits growth of the microorganism as detected by the unaided eye are taken as MIC.

Example 18. Cytochrome $P_{450}3A4$ Inhibition Assay for Determining $IC_{50}$ The potential of the compound to inhibit CYP 3A4 was tested by the LC-MS/MS based probe substrate method using human liver microsomes. Midazolam or testosterone, which are metabolized to hydroxymidazolam or hydroxytestosterone by CYP 3A4, were the probe substrates used. Serial dilutions of the compound ranging from 50 µM to 0.69 µM was incubated in 0.1 mg/mL human liver microsomes in the presence of 5 µM midazolam or 50 µM testosterone. NADPH was added as the cofactor. Samples containing no test compound were incubated in parallel as the basal control with no enzyme inhibition. After incubation for ten minutes, the amount of 1-hydroxymidazolam or 6β-hydroxyltestosterone formed was determined by LC-MS/MS method as a measure of enzyme activity. Percent inhibition of enzyme activity was calculated based on the amount of metabolites (1-hydroxymidazolam or 6β-hydroxyltestosterone) formed for each sample relative to the basal control and plotted in a curve versus the compound concentration to obtain the IC50.

Example 19. Test Results

The results of minimum inhibitory concentration (MIC) and $IC_{50}$ of cytochrome $P_{450}3A4$ inhibition of test compounds are shown in the table below. Compounds 13F, solithromycin, clindamycin, and ketoconazole are included for comparative purposes. Compounds with low MIC and high $IC_{50}$ for CYP3A4 are desired.

TABLE 1

| N-R of Formula I | | ATCC49619 QC strain | AUCC 479 penS, macS | MIC (µg/ml) Strep. Pneumoniae AUCC 488 penR, macR M or iMLS | AUCC 489 penR, macR cMLS | AUCC 483 penS, macR cMLS | IC50 (µM) CYP3A4 (midazolam) | IC50 (µM) CYP3A4 (testosterone) |
|---|---|---|---|---|---|---|---|---|
| | | | | Compound | | | | |
| 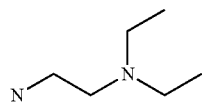 | 13A | 0.015-0.06 | 0.008-0.015 | 0.12-0.25 | 0.12-0.25 | 0.12-0.25 | 1.2 | |

TABLE 1-continued
| N-R of Formula I | | ATCC49619 QC strain | AUCC 479 penS, macS | MIC (μg/ml) Strep. Pneumoniae AUCC 488 penR, macR M or iMLS | AUCC 489 penR, macR cMLS | AUCC 483 penS, macR cMLS | IC50 (μM) CYP3A4 (midazolam) | IC50 (μM) CYP3A4 (testosterone) |
|---|---|---|---|---|---|---|---|---|
| 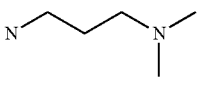 | 13B | 0.015-0.03 | 0.008-0.015 | 0.12-0.25 | 0.12-0.25 | 0.12-0.25 | 6.4 | |
| 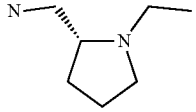 | 13C | 0.06-0.12 | 0.03 | 0.5 | 0.5-1 | 0.5-1 | 1.8 | |
| 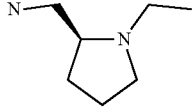 | 13D | 0.03-0.06 | 0.015-0.03 | 0.25-0.5 | 0.12-0.25 | 0.25-0.5 | 2.9 | |
| 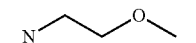 | 13E | 0.06-0.12 | 0.03-0.06 | 0.25-0.5 | >4 | >4 | Not Tested | |
| 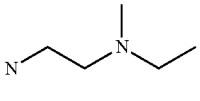 | 13G | 0.12-0.25 | 0.03-0.06 | 0.5-1 | 0.5-1 | 1-2 | 8.8 | |
| 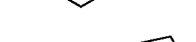 | 13H | 0.03-0.06 | 0.008-0.015 | 0.25-1 | 0.25-1 | 2-4 | 1.9 | |
| 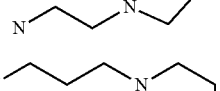 | 13I | 0.03-0.06 | 0.015-0.03 | 0.25-0.5 | 0.25-1 | 0.25-1 | 2.1 | |
| 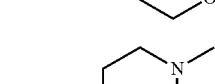 | 13J | 0.06-0.12 | 0.03-0.06 | 1 | 1-2.0 | 0.5-2 | 5.9 | |
| 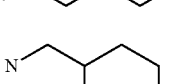 | 13K | 0.06-0.12 | 0.03-0.06 | 1 | 0.5-1 | 0.5-1 | 6.5 | |
| 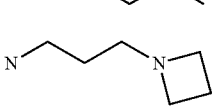 | 13L | 0.06 | 0.03 | 0.5-1 | 0.5-1 | 0.5-1 | 6.3 | |
| 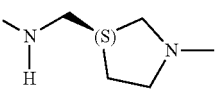 | 13M | 0.03-0.06 | 0.015-0.03 | 0.5-1 | 0.25-0.5 | 0.25-0.5 | 10.3 | |
| 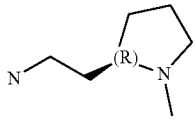 | 13N | 0.03-0.06 | 0.03 | 0.5-1 | 0.5-1 | 0.5-1 | 7.7 | |
| 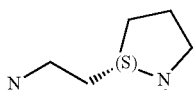 | 13P | 0.03-0.06 | 0.015-0.03 | 0.5-1 | 0.12-0.25 | 0.06-0.12 | 6.3 | |
|  | 13Q | 0.03-0.06 | 0.015-0.03 | 0.5-1 | 0.12-0.25 | 0.12-0.25 | 4.8 | |

TABLE 1-continued

| N-R of Formula I | | ATCC49619 QC strain | AUCC 479 penS, macS | MIC (µg/ml) Strep. Pneumoniae AUCC 488 penR, macR M or iMLS | AUCC 489 penR, macR cMLS | AUCC 483 penS, macR cMLS | IC50 (µM) CYP3A4 (midazolam) | IC50 (µM) CYP3A4 (testosterone) |
|---|---|---|---|---|---|---|---|---|
| Comparative Compound | | | | | | | | |
| [structure] | 13F | 0.015-0.06 | 0.0015 | 0.25 | 0.12-0.25 | 0.25-0.5 | 1.1 | |
| | solithromycin | 0.004-0.015 | 0.004-0.015 | 0.06-0.25 | 0.004-0.008 | 0.008-0.015 | 0.4 | 1.49 |
| | erythromycin | 0.03-0.06 | 0.03-0.06 | 8-16 | 8-32 | 64 | | |
| | clindamycin | 0.06 | 0.015-0.03 | 0.06 | >64 | ≥64 | | |
| | ketoconazole | | | | | | 0.013 | |

The results of Table 1 show that compounds of the present invention, i.e., Compounds 13A, 13B, 13C, 13D, 13G, 13H, 13I, 13J, 13K, 13L, 13M, 13N, 13P, and 13Q all have lower IC50 inhibition of CYP3A4 inhibition in comparison with solithromycin, and ketoconazole. Thus, the compounds of the present invention have reduced drug-drug interactions and have improved the safety of co-administration with other drugs.

Compounds of the present invention display MIC activity in strains previously characterized as macrolide-resistant and/or penicillin-resistant. The compounds of the present invention show superior MIC activity compared to erythromycin in the strains of AUCC488 and AUCC489, both macrolide-resistant and penicillin-resistant, and in the strain of AUCC483, macrolide-resistant and penicillin-resistant sensitive. The new compounds were also superior to clindamycin in terms of MIC in the AUCC489 AUCC483 strains.

It is to be understood that the foregoing describes preferred embodiments of the present invention and that modifications may be made therein without departing from the scope of the present invention as set forth in the claims.

What is claimed is:

1. A compound having Formula I, or a pharmaceutically acceptable salt thereof,

Formula I

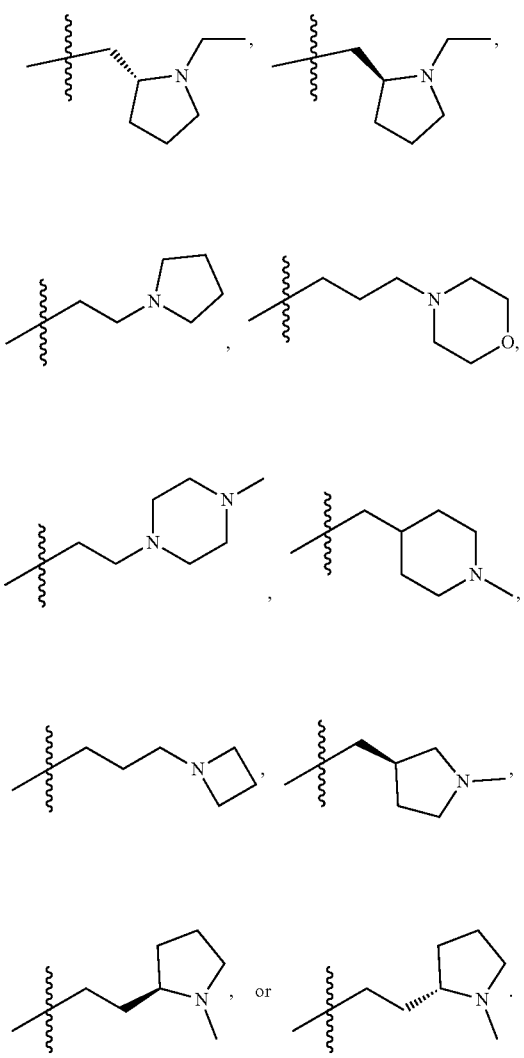

wherein R is —(CH$_2$)$_3$N(CH$_3$)$_2$, —(CH$_2$)$_2$N(CH$_2$CH$_3$)$_2$, —(CH$_2$)$_2$OCH$_3$, —(CH$_2$)$_2$N(CH$_2$CH$_3$)(CH$_3$), —CH$_2$CN, 2. The compound according to claim 1, wherein said compound is

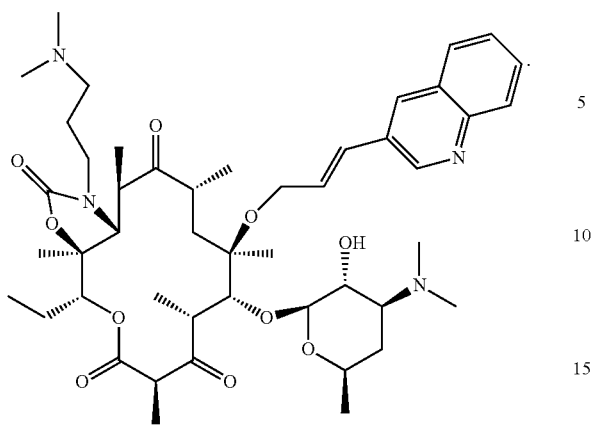

3. A pharmaceutical composition comprising a pharmaceutically acceptable carrier and the compound of claim 1, or a pharmaceutically acceptable salt thereof.

4. The pharmaceutical composition according to claim 3, wherein the composition is in an oral form of tablets, capsules, granules, powders, or syrups.

5. A method of treating antimicrobial infection, comprising the steps of:
   administering to a subject suffering from antimicrobial infection the compound of claim 1, or a pharmaceutically acceptable salt thereof, in an amount effective to treat antimicrobial infection.

* * * * *